US009523108B2

(12) United States Patent
Okuma et al.

(10) Patent No.: US 9,523,108 B2
(45) Date of Patent: Dec. 20, 2016

(54) THERMOSTABLE β-XYLOSIDASE

(71) Applicant: HONDA MOTOR CO., LTD., Minato-Ku, Tokyo (JP)

(72) Inventors: Jiro Okuma, Wako (JP); Migiwa Suda, Wako (JP); Asuka Yamaguchi, Wako (JP); Yoshitsugu Hirose, Wako (JP); Yasuhiro Kondo, Wako (JP); Masaru Sato, Kisarazu (JP); Daisuke Shibata, Kisarazu (JP)

(73) Assignee: Honda Motor Co., Ltd., Tokyo (JP)

( * ) Notice: Subject to any disclaimer, the term of this patent is extended or adjusted under 35 U.S.C. 154(b) by 0 days.

(21) Appl. No.: 14/962,926

(22) Filed: Dec. 8, 2015

(65) Prior Publication Data

US 2016/0168548 A1   Jun. 16, 2016

(30) Foreign Application Priority Data

Dec. 12, 2014   (JP) ................. 2014-252069

(51) Int. Cl.
| | | |
|---|---|---|
| *C12N 9/26* | (2006.01) | |
| *C12P 19/02* | (2006.01) | |
| *C12P 19/14* | (2006.01) | |
| *C12N 9/24* | (2006.01) | |

(52) U.S. Cl.
CPC ............. *C12P 19/02* (2013.01); *C12N 9/2402* (2013.01); *C12P 19/14* (2013.01); *C12Y 302/01037* (2013.01)

(58) Field of Classification Search
CPC .............. C12N 9/2434; C12P 9/02; C12P 9/14
See application file for complete search history.

(56) References Cited

U.S. PATENT DOCUMENTS 7,923,234 B2 * 4/2011 Thompson ....... C12Y 302/0103
435/200
8,609,376 B2 * 12/2013 Mitsuzawa ............. C12P 19/02
435/99
2012/0003702 A1 * 1/2012 Mitsuzawa ............. C12P 19/02
435/99

FOREIGN PATENT DOCUMENTS

| JP | H11-507837 A | 7/1999 |
|---|---|---|
| JP | 11-313683 A | 11/1999 |
| JP | 2001-523346 A | 8/2011 |
| JP | 2013-059272 A | 4/2013 |
| WO | 97/00964 A1 | 1/1997 |
| WO | 2009/094187 A1 | 7/2009 |

OTHER PUBLICATIONS

Branden et al. Introduction to Protein Structure, Garland Publishing Inc., New York, p. 247, 1991.*
Q9WXT1—UniProtKB Database. 1999.*
Kormelink et al., "Purification and Characterization of Three Endo-(1, 4)-Beta-Xylanases and One Beta-Xylosidase From Aspergillus awamori", Journal of Biotechnology, 1993, vol. 27, pp. 249-265.
Herrmann et al., "the Beta-D-xylosidase of Trichoderma reesei is a multifunctional Beta-D-xylan xylohydrolase", Biochemical Journal, 1997, vol. 321, pp. 375-381.
Kitamoto et al., "Sequence Analysis, Overexpression, and Antisense Inhibition of a Beta-Xylosidase Gene, xylA, from Aspergillus oryzae KBN616", Applied and Environmental Microbiology, 1999, vol. 65, pp. 20-24.
La Grange et al., "Degradation of Xylan to D-Xylose by Recombinant Saccharomyces cerevisiae Coexpressing the Aspergillus niger Beta-Xylosidase (xlnD) and the Trichoderma reesei Xylanase II (xyn2) Genes", Applied and Environmental Microbiology, 2001, vol. 67, pp. 5512-5519.
Shao et al., "Characterization of a Novel Beta-Xylosidase, XylC, from Thermoanaerobacterium saccharolyticum JW/SL-YS485", Applied and Environmental Microbiology, 2011, vol. 77, pp. 719-726.
Morais et al., "Functional Association of Catalytic and Ancillary Modules Dictates Enzymatic Activity in Glycoside Hydrolase Family 43 Beta-Xylosidase", Journal of Biological Chemistry, 2012, vol. 287, pp. 9213-9221.
Shi et al., "Biochemical properties of a novel thermostable and highly xylose-tolerant Beta-xylosidase/alpha-arabinosidase from Thermotoga thermarum", Biotechnology for Biofuels, 2013, vol. 6, No. 27.
Noguchi et al., "MetaGeneAnnotator: Detecting Species-Specific Patterns of Ribosomal Binding Site for Precise Gene Prediction in Anonymous Prokaryotic and Phage Genomes", DNA Research, 2008, vol. 15, pp. 387-396, Chiyoda-ku, Tokyo, Japan.
Finn et al., "The Pfam protein families database", Nucleic Acids Research, 2010, vol. 38, pp. D211-D222, Helsinki, Finland.
Durbin et al., Biological sequence analysis: Probabilistic models of proteins and nucleic acids, 1998, Cambridge University Press.
Suzuki et al., "Screening of a Mutant Plasmid with Hifgh Expression Efficiency of GC-Rich leuB Gene of an Extreme Thermophile, Thermus thermophilus, in *Escherichia coli*", J. Biochem., 1997, vol. 121, pp. 1031-1034.
Ishida et al., "Effective Structure of a Leader Open Reading Frame for Enhancing the Expression of GC-Rich Genes", J. Biochem., 2002, vol. 132, pp. 63-70.
Extended European search report issued in corresponding EP patent application 15198608.0 with a mailing date of Apr. 8, 2016.

(Continued)

*Primary Examiner* — Yong Pak
(74) *Attorney, Agent, or Firm* — Carrier Blackman & Associates, P.C.; William D. Blackman; Fulchand P. Shende

(57) ABSTRACT

A thermostable β-xylosidase, having a β-xylosidase catalytic domain including: (A) a polypeptide including the amino acid sequence represented by SEQ ID NO: 1 or 2, (B) a polypeptide including an amino acid sequence in which at least one amino acid has been deleted, substituted, or added in the amino acid sequence represented by SEQ ID NO: 1 or 2, and having hydrolysis activity against a substrate of p-nitrophenyl-β-D-xylopyranoside at least under conditions of 105° C. and pH 5.0, or (C) a polypeptide including an amino acid sequence having 75% or greater sequence identity with the amino acid sequence represented by SEQ ID NO: 1 or 2, and having hydrolysis activity against a substrate of p-nitrophenyl-β-D-xylopyranoside at least under conditions of 105° C. and pH 5.0.

4 Claims, 7 Drawing Sheets

(56) References Cited

OTHER PUBLICATIONS

Anand et al., "Characteristics of thermostable endoxylanase and Beta-xylosidase of the extremely thermophilic bacterium Geobacillus thermodenitrificans TSAA1 and its applicability in generating xylooligosaccharides and xylose from agro-residues", Extremophiles, vol. 17, No. 3, Mar. 16, 2013, pp. 357-366, XP055260303, JP ISSN: 1431-0651, DOI:10.1007/s00792-013-0524-x.

Database UniProt [Online] Jun. 28, 2011, "SubName: Full=Glycoside hydrolase family 3 domain protein {ECO:0000313:EMBL:AEE97239.1},", XP002755750, retrieved from EBI accession No. UNIPROT:F4A2H3 Database accession No. F4A2H3.

Database UniProt [Online] Nov. 25, 2008, "Subname: Full=Xylosidase/arabinosidase {ECO:0000313:EMBL:ACI20082.1};",XP002755751, retrieved from EBI accession No. UNIPROT:B5YAF8 Database accession No. B5YAF8.

* cited by examiner

```
OJ1M-273    1057 GTGTTGCTCAAAAACGATGGTAACTTGCTTCCGCTACGAAAAGATTTGTCAAGCATCGCCGTCATCGGTTCCAAAC 1131
OJ1M-273-1  1126 GTGTTGCTCAAAAACGATGGTAACTTGCTTCCGCTACGAAAAGATTTGTCAGCATCGCCGTCATCGGTTCCAAAC 1200

OJ1M-273    1132 GCCGACGACCACGAAACATGCTCGGCGATTACGCTTATGTGGCTCACTTGGACTTGAAGGAAACGCCTGTGCCA 1096
OJ1M-273-1  1201 GCCGACGACCACGAAACATGCTCGGCGATTACGCTTATGTGGCTCACTTGGACTTGAAGGAAACGCCTGTGCCA 1275

OJ1M-273    1197 ATTGTGACTGTCCTTGAAGGCATCAAGGCGAAAGTTTCGCCCGGCCACGAAAGTCCTCTACGCCAAAGGTTGCGAA 1281
OJ1M-273-1  1276 ATTGTGACTGTCCTTGAAGGCATCAAGGCGAAAGTTTCACCCGGCCACGAAAGTCCTTACGCCAAAGGTTGCGAA 1350

OJ1M-273    1282 GTTCTGGACGGGACAACGGAAGGAATCGCCGAAGGCGGTTGAAGTCGCAAAACAAGCGGAAGTCGTGTCTTGGTC 1356
OJ1M-273-1  1351 GTTCTGGACGGGACAACGGAAGGAATCGCCGAAGGCGGTTGAAGTCGCAAAACAAGCGGAAGTCGTGTCTTGGTC 1425

OJ1M-273    1357 GTCGGTGACCGCTCAGGCTTGTTCGGCAAGGCTTGTTCGGCAAAGGGACGGTCGGCGAAGGTTGCGATAGGGTTGACTTGAGGCTTCCC 1431
OJ1M-273-1  1426 GTCGGTGACCGCTCAGGCTTGTTCGGCAAGGCTTGTTCGGCAAAGGGACGGTCGGCGAAGGTTGCGATAGGGTTGACTTGAGGCTTCCC 1500

OJ1M-273    1432 GGTCACCAAGAGGAACTTGTCAAGGCTGTGTTGGTTGAAACTTCCGGCAATAGTTGAGGCTTGGTTCTCTCATCAACGGTCGC 1496
OJ1M-273-1  1501 GGTCACCAAGAGGAACTTGTCAAGGCTGTGTTGGTTGAAACTTCCGGCAATAGTTGAGGCTTGGTTCTCTCATCAACGGTCGC 1575

OJ1M-273    1497 CCCGTTACGCTTGGAAGAACTCGTTGACAAAATTCCGGCACAGTCGGCGCAAACTCCCATCACCTTCCGAAAGTCGTC 1581
OJ1M-273-1  1576 CCCGTTACGCTTGGGGGAACTCGTTGACAAAATTCCGGCACAGTCGGCGCAAACTCCCATCACCTTCCGAAAGTCGTC 1650

OJ1M-273    1582 AATGCTGTCGCTGATGTTTTGTTGTTGGCATATAGCCGAGCACCGCTTTCGCACCGGCGATTATGTGGAGATGAAAAATGTCCCGCAA 1656
OJ1M-273-1  1651 AATGCTGTCACTGATGTTTTGTTGTTGGCATATAGCCGAGCACCGCTTTCGCACCGGCGATTATGTGGAGATGAAAAATGTCCCGCAA 1725

OJ1M-273    1657 GGTCAAGTCCCGCTGCACTATAGCCGAGCACCGCTTTCGCACCGGCGATTATGTGGAGATGAAAAATGTCCCGCAA 1731
OJ1M-273-1  1726 GGTCAAGTCCCGCTGCACTATAGCCGAGCACCGCTTTCGCACCGGCGATTATGTGGAGATGAAAAATGTCCCGCAA 1800

OJ1M-273    1732 TTCCCATTCGGGCACGGGCTCAGTTGACGAAGTTGAATACAGCGACTTGAATACAGCGACTTGCCCTGAGAAAATTTCA 1796
OJ1M-273-1  1801 TTCCCATTCGGGCACGGGCTCAGTTGACGAAGTTGAATACAGCGACTTGAATACAGCGACTTGCCCAGAGAAAATTTCA 1875

OJ1M-273    1797 CCCGCAGGCACAGTCTCCATCTCCGTGACGGTCGGCGACCGGACCGAGAAGGTGACGAGGTTGTCCAGTTG 1881
OJ1M-273-1  1876 CCCGCAGGCACAGTCTCCATCTCCGTGACGGTCGGCGACCGGACCGAGAAGGTGATGAGGTTGTCCAGTTG 1950

OJ1M-273    1882 TATGTCCGCGATGTCGCAAGCCGCGTCCGACCGTCGGCAAGGAACTCAAGGTTTCAAGCGAGTGACGCTGAAG 1956
OJ1M-273-1  1951 TATGTCCGCGATGTAGCAAGCCGCGTCCGACCGTCGGCAAGGAACTCAAGGTTTCAAGCGAGTGACGCTGAAG 2025

OJ1M-273    1957 CCAGGTGAGGTCTAAACGGGTGACTTTCCACCTGTCCGCTGACCAGTTGGCTTTTTACGACCGAGCGATGAGGTTC 2031
OJ1M-273-1  2026 CCAGGTGAGGTCTAAACGGGTGACTTTCCACCTGTCCGCTGACCAGTTGGCTTTTTACGACCGAGCGATGAGGTTC 2100

OJ1M-273    2032 GTGGGTTGAGCCAGGAACAATTGAGGTCATGTCGTCTGAGGACTCGTCTGAGGACATAGGCTCACCGGCAAATTTGAA 2096
OJ1M-273-1  2101 GTGGGTTGAGCCAGGAACAATTGAGGTCATGTCGTCTGAGGACTCGTCTGAGGACATCAGGCTCACCGGCAAATTTGAA 2175

OJ1M-273    2097 ATTGTCGGCGATGTCAGGTGAAAGGGTCATGTTCACTCGGGTTGAAGTTGAGCCGCATGA 2178
OJ1M-273-1  2176 ATTGTCGGCGATGTCAGGTGAAAGGGTCATGTTCACTCAGGTTGAAGTTGAGCCGCATGA 2247
```

FIG. 2

```
OJ1M-273     1 MSVRVKELLAKMTLEEKVAQLGSISVHRLMTDGKFDIAKARELLKHGIGQITRVAGGSNLPPKEAAQLANEIQRFLIEET  80
OJ1M-273-1   1 MSVRVKELLAKMTLEEKVAQLGSISVHRLMTDGKFDIAKARELLKHGIGQITRVAGGSDLPPKEAAQLANEIQRFLIEET  80

OJ1M-273    81 RLGIPAIVHEECLSGLMARGSTTFPQAINLASTFDPDLVREMTTVIRKEMRAVGAHQGLSPVLDVLRDPRWGRTEETFGE 160
OJ1M-273-1  81 RLGIPAIVHEECLSGLMARGSTTFPQAINLASTFDPDLVREMTTVIRKEMRAVGAHQGLSPVLDVLRDPRWGRTEETFGE 160

OJ1M-273   161 DPYLIACMAVAYISGLQGEDLRQGVIATAKHFSGHGWPEGGRNCAPLHVGPREFREVLSFPFEAAVRVARVQSVMNAYHD 240
OJ1M-273-1 161 DPYLIACMAVAYISGLQGEDLRQGVIATAKHFSGHGWPEGGRNCAPLHVGPREFREVLSFPFEAAVRVARVQSVMNAYHD 240

OJ1M-273   241 IDGIPCAASRELLTDLLRGEWGFDGIVVSDYAAVHMLFNVHRVAVDEKDAACQALYAGIXXXXXXXXXXXXXXXXX---- 318
OJ1M-273-1 241 IDGIPCAASRELLTDLLRGEWGFDGIVVSDYAAVHMLFNVHRVAVDEKDAACQALYAGIDIELPDLNCYAKLIDAVREGL 320

OJ1M-273   319 ------------LFDNPPFVDPEAAPSVFDAPEHRQLARLLAQKSIVLLKNDGNLLPLRKDLSIAVIGPN 377
OJ1M-273-1 321 ISEAIVDEAVRRVLTVKERLGLFDNPPFVDPEAAPSVFDAPEHRQLARLLAQKSIVLLKNDGNLLPLRKDLSGIAVIGPN 400

OJ1M-273   378 ADDPRNMLGDYAYVAHLDKETPVPIVTVLEGIKAKVSPATKVLYAKGCEVLDGTTEGIAEAVEVAKQAEVVVLVVGDRS 457
OJ1M-273-1 401 ADDPRNMLGDYAYVAHLDKETPVPIVTVLEGIKAKVSPATKVLYAKGCEVLDGTTEGIAEAVEVAKQAEVVVLVVGDRS 480

OJ1M-273   458 GLFGKGTVGEGCDRVDLRLPGHQEELVKAVVETGKPVVLVLINGRPVTLGELVDKIPAIVEAWFPGEEGGNAVADVLFGD 537
OJ1M-273-1 481 GLFGKGTVGEGCDRVDLRLPGHQEELVKAVVETGKPVVLVLINGRPVTLGELVDKIPAIVEAWFPGEEGGNAVADVLFGD 560

OJ1M-273   538 VNPGGKLPITFPKVVGQVPLHYSRAPLSHRDYVEMKNVPQFPFGHGLSYTKFEYSDLTIAPEKISPAGTVSISVTVKNVG 617
OJ1M-273-1 561 VNPGGKLPITFPKVVGQVPLHYSRAPLSHRDYVEMKNVPQFPFGHGLSYTKFEYSDLTIAPEKISPAGTVSISVTVKNVG 640

OJ1M-273   618 DREGDEVVQLYVRDDVVASRVRPVKELKGFKRVTLKPGEAKRVTFHLSADQLAFYDRAMRFVVEPGTIEVMVGSSSEDIRL 697
OJ1M-273-1 641 DREGDEVVQLYVRDDVVASRVRPVKELKGFKRVTLKPGEAKRVTFHLSADQLAFYDRAMRFVVEPGTIEVMVGSSSEDIRL 720

OJ1M-273   698 TGKFEIVGDVREVPGERVMFTRVEVEPA 725
OJ1M-273-1 721 TGKFEIVGDVREVPGERVMFTQVEVEPA 748
```

FIG. 3

THERMOSTABLE β-XYLOSIDASE

TECHNICAL FIELD

The present invention relates to a thermostable β-xylosidase, a polynucleotide encoding the thermostable β-xylosidase, an expression vector for expressing the thermostable β-xylosidase, a transformant into which the expression vector has been incorporated, and a method for producing a lignocellulose degradation product using the thermostable β-xylosidase.

Priority is claimed on Japanese Unpublished Patent Application No. 2014-252069, filed Dec. 12, 2014, the content of which is incorporated herein by reference.

BACKGROUND ART

In recent years, as a result of concerns related to energy supplies for transportation, as well as other environmental problems such as global warming and aerial pollution, the development of alternative energy sources to oil has become an extremely important issue. Plant biomass is the most plentiful renewable energy source on earth, and holds great promise as an alternative energy source to oil. The main component of plant biomass is lignocellulose, which is composed of polysaccharides such as celluloses and hemicelluloses (including xylan, arabinan and mannan), and lignin. These polysaccharides are hydrolyzed by a large variety of glycoside hydrolases to form monosaccharides such as glucose and xylose, which can then be used as biofuels or the raw materials for chemical products.

Lignocellulose is recalcitrant due to its highly complex structure, and is difficult to degrade or hydrolyze with a single enzyme. Accordingly, among the various polysaccharides, hydrolysis of cellulose generally requires three types of glycoside hydrolase enzymes, namely an endoglucanase (endo-1,4-β-D-glucanase, EC 3.2.1.4), an exo-type cellobiohydrolase (1,4-β-cellobiosidase or cellobiohydrolase, EC 3.2.1.91, EC 3.2.1.176), and a β-glucosidase (EC 3.2.1.21). On the other hand, the structure of hemicellulose varies depending on the plant, and for example in the case of hardwoods and herbaceous plants, xylan is the main structural component. Hydrolysis of xylan requires a xylanase (endo-1,4-β-xylanase, EC 3.2.1.8) and a β-xylosidase (3.2.1.37). β-xylosidase is a hydrolase involved in the process of hydrolyzing the oligosaccharides, which are generated by hydrolysis of the hemicellulose by xylanase, to produce monosaccharides.

In conventional bioethanol production using lignocellulose as a starting resource, hydrolysis processes using high solid loading (30 to 60% solid loading) have been tested with the aim of achieving a more energy-efficient conversion to ethanol. However, in this type of lignocellulose enzymatic hydrolysis using high solid loading, the viscosity of the hydrolyzed biomass solution is high, and the hydrolysis reaction of the lignocellulose tends to proceed poorly. Accordingly, by using a thermostable enzyme and performing the enzymatic hydrolysis process at a high temperature, for example 80° C. or higher, the rate of the hydrolysis reaction can be increased, and the viscosity of the hydrolyzed biomass solution can be reduced, which is expected to enable a shortening of the hydrolysis reaction time and a reduction in the amount of enzyme required. As a result, for all of the various glycoside hydrolases, the development of enzymes having superior thermal stability is very desirable.

Many thermostable glycoside hydrolases have been obtained by isolating and identifying thermophilic microorganisms that exist in high-temperature environments, cloning genes from these isolated and cultured microorganisms, determining the DNA sequence, and then expressing the DNA using *E. coli* or filamentous fungi or the like. For example, Patent Document 1 discloses a β-xylosidase derived from a filamentous fungus. Patent Document 2 discloses a β-xylosidase derived from the filamentous fungus *Aspergillus oryzae*, the β-xylosidase exhibiting enzymatic activity at 30° C. Patent Document 3 discloses a β-xylosidase derived from *Alicyclobacillus acidocaldarius*, the β-xylosidase exhibiting enzymatic activity at pH 5.5 or lower and temperatures of 50° C. or higher. Patent Document 4 discloses a β-xylosidase derived from *Acremonium cellulolyticus*, the β-xylosidase exhibiting enzymatic activity at 45° C. Further, Non-Patent Documents 1 to 6 disclose β-xylosidases isolated from specific bacteria and filamentous fungi, including β-xylosidases having an optimum temperature in the vicinity of 60° C. In addition, Non-Patent Document 7 reports a thermostable 1-xylosidase having an optimum temperature of 95° C. However, although the catalytic efficiency Kcat/Km of the enzyme when p-nitrophenyl-β-D-xylopyranoside (hereafter often abbreviated as PNPX) is used as a substrate is an extremely high value of 1173.4 $mM^{-1}s^{-1}$, the half life of the PNPX degradation activity at 90° C. is about 30 minutes, indicating that the thermal stability is insufficient.

PRIOR ART LITERATURE

Patent Documents

Patent Document 1: Published Japanese Translation No. Hei 11-507837 of PCT International Publication
Patent Document 2: Japanese Unexamined Patent Application, First Publication No. Hei 11-313683
Patent Document 3: Published Japanese Translation No. 2011-523346 of PCT International Publication
Patent Document 4: Japanese Unexamined Patent Application, First Publication No. 2013-59272

Non-Patent Documents

Non-Patent Document 1: Kormelink et al., Journal of Biotechnology, 1993, vol. 27, pp. 249 to 265.
Non-Patent Document 2: Herrmann et al., Biochemical Journal, 1997, vol. 321, pp. 375 to 381.
Non-Patent Document 3: Kitamoto et al., Applied and Environmental Microbiology, 1999, vol. 65, pp. 20 to 24.
Non-Patent Document 4: La Grange et al., Applied and Environmental Microbiology, 2001, vol. 67, pp. 5512 to 5519.
Non-Patent Document 5: Shao et al., Applied and Environmental Microbiology, 2011, vol. 77, pp. 719 to 726.
Non-Patent Document 6: Morais et al., Journal of Biological Chemistry, 2012, vol. 287, pp. 9213 to 9221.
Non-Patent Document 7: Shi et al., Biotechnology for Biofuels, 2013, vol. 6, No. 27.

SUMMARY OF THE INVENTION

Problems to be Solved by the Invention

The present invention has an object of providing a novel thermostable β-xylosidase that exhibits hydrolysis activity against a substrate of PNPX at least under conditions of 105° C. and pH 5.0, a polynucleotide encoding the thermostable β-xylosidase, an expression vector for expressing the thermostable β-xylosidase, a transformant into which the expression vector has been incorporated, and a method for producing a lignocellulose degradation product using the thermostable β-xylosidase.

Means for Solving the Problem

In order to achieve the above object, the inventors of the present invention extracted DNA directly from the high-temperature soils of hot springs, and by carrying out large-scale metagenomic sequencing of the microbial flora that was difficult to culture, they succeeded in obtaining a thermostable β-xylosidase having a novel amino acid sequence, thus enabling them to complete the present invention.

In other words, a thermostable β-xylosidase, a polynucleotide, an expression vector, a transformant, a method for producing the thermostable β-xylosidase, a glycoside hydrolase mixture, and a method for producing a lignocellulose degradation product according to the present invention have the aspects [1] to [10] described below.

[1] A thermostable β-xylosidase, having a β-xylosidase catalytic domain including:
(A) a polypeptide including the amino acid sequence represented by SEQ ID NO: 1 or 2,
(B) a polypeptide including an amino acid sequence in which at least one amino acid has been deleted, substituted, or added in the amino acid sequence represented by SEQ ID NO: 1 or 2, and having hydrolysis activity against a substrate of p-nitrophenyl-β-D-xylopyranoside at least under conditions of 105° C. and pH 5.0, or
(C) a polypeptide including an amino acid sequence having 75% or greater sequence identity with the amino acid sequence represented by SEQ ID NO: 1 or 2, and having hydrolysis activity against a substrate of p-nitrophenyl-β-D-xylopyranoside at least under conditions of 105° C. and pH 5.0.

[2] The thermostable β-xylosidase according to [1], which also exhibits at least one activity selected from the group consisting of α-L-arabinofuranosidase activity and α-L-arabinopyranosidase activity.

[3] A polynucleotide, having a region encoding a β-xylosidase catalytic domain, the region including:
(a) a nucleotide sequence encoding a polypeptide including the amino acid sequence represented by SEQ ID NO: 1 or 2,
(b) a nucleotide sequence encoding a polypeptide which includes an amino acid sequence in which at least one amino acid has been deleted, substituted, or added in the amino acid sequence represented by SEQ ID NO: 1 or 2, and has hydrolysis activity against a substrate of p-nitrophenyl-β-D-xylopyranoside at least under conditions of 105° C. and pH 5.0,
(c) a nucleotide sequence encoding a polypeptide which includes an amino acid sequence having 75% or greater sequence identity with the amino acid sequence represented by SEQ ID NO: 1 or 2, and has hydrolysis activity against a substrate of p-nitrophenyl-β-D-xylopyranoside at least under conditions of 105° C. and pH 5.0,
(d) a nucleotide sequence, having 80% or greater sequence identity with a nucleotide sequence represented by SEQ ID NO: 3 or 4, and encoding a polypeptide that has hydrolysis activity against a substrate of p-nitrophenyl-β-D-xylopyranoside at least under conditions of 105° C. and pH 5.0, or
(e) a nucleotide sequence of a polynucleotide which hybridizes under stringent conditions with a polynucleotide including the nucleotide sequence represented by SEQ ID NO: 3 or 4, the nucleotide sequence encoding a polypeptide having hydrolysis activity against a substrate of p-nitrophenyl-β-D-xylopyranoside at least under conditions of 105° C. and pH 5.0.

[4] The polynucleotide according to [3], wherein the polypeptide also exhibits at least one activity selected from the group consisting of α-L-arabinofuranosidase activity and α-L-arabinopyranosidase activity.

[5] An expression vector incorporating the polynucleotide according to [3] or [4], the expression vector being capable of expressing a polypeptide having β-xylosidase activity in a host cell.

[6] A transformant into which the expression vector according to [5] has been introduced.

[7] The transformant according to [6], which is a eukaryote.

[8] A method for producing a thermostable β-xylosidase, the method including generating the thermostable β-xylosidase in the transformant according to [6] or [7].

[9] A glycoside hydrolase mixture, including the thermostable β-xylosidase according to [1] or [2], a thermostable β-xylosidase encoded by the polynucleotide according to [3] or [4], or a thermostable β-xylosidase produced by the method for producing a thermostable β-xylosidase according to [8], and at least one other glycoside hydrolase.

[10] A method for producing a lignocellulose degradation product, the method including generating the lignocellulose degradation product by bringing a material containing lignocellulose into contact with the thermostable β-xylosidase according to [1] or [2], a thermostable β-xylosidase encoded by the polynucleotide according to [3] or [4], the transformant according to [6] or [7], a thermostable β-xylosidase produced by the method for producing a thermostable β-xylosidase according to [8], or the glycoside hydrolase mixture according to [9].

Effects of the Invention

The thermostable β-xylosidase according to the present invention has hydrolysis activity against a substrate of PNPX at least under conditions of 105° C. and pH 5.0. For this reason, the thermostable β-xylosidase is suitable for hydrolysis processes of materials containing lignocellulose under high-temperature conditions.

Further, in another aspect of the present invention, the thermostable β-xylosidase is suitable for hydrolysis processes of materials containing compounds having β-xylosidic bonds under high-temperature conditions. These materials containing compounds having β-xylosidic bonds can be obtained, for example, by hydrolysis of lignocellulose materials containing hemicellulose using a xylanase.

Moreover, in yet another aspect of the present invention, the thermostable β-xylosidase is suitable for hydrolysis processes of materials containing arabinose residues, and specifically arabinofuranose residues or arabinopyranose residues.

Furthermore, the polynucleotide according to the present invention, an expression vector incorporating the polynucleotide, and a transformant into which the expression vector has been introduced can be used favorably in the production of the thermostable β-xylosidase according to the present invention.

BRIEF DESCRIPTION OF THE DRAWINGS

FIG. 1A is an alignment diagram (first half) of the nucleotide sequence (SEQ ID NO: 3) of an open reading frame OJ1M-273 and the nucleotide sequence (SEQ ID NO: 4) of a β-xylosidase candidate gene OJ1-273-1.

FIG. 1B is an alignment diagram (second half, continuation of FIG. 1A) of the nucleotide sequence (SEQ ID NO: 3) of the open reading frame OJ1M-273 and the nucleotide sequence (SEQ ID NO: 4) of the β-xylosidase candidate gene OJ1-273-1.

FIG. 2 is an alignment diagram of the amino acid sequence (SEQ ID NO: 1) of the open reading frame OJ1M-273 and the amino acid sequence (SEQ ID NO: 2) of the β-xylosidase candidate gene OJ1-273-1.

FIG. 3 is an alignment diagram of the amino acid sequence (SEQ ID NO: 2) of the β-xylosidase candidate gene OJ1-273-1 and the amino acid sequence (SEQ ID NO: 9) of the β-xylosidase of *Candidatus Caldatribacterium californiense*.

DETAILED DESCRIPTION OF THE INVENTION

[Thermostable β-Xylosidase]

Figure 4:
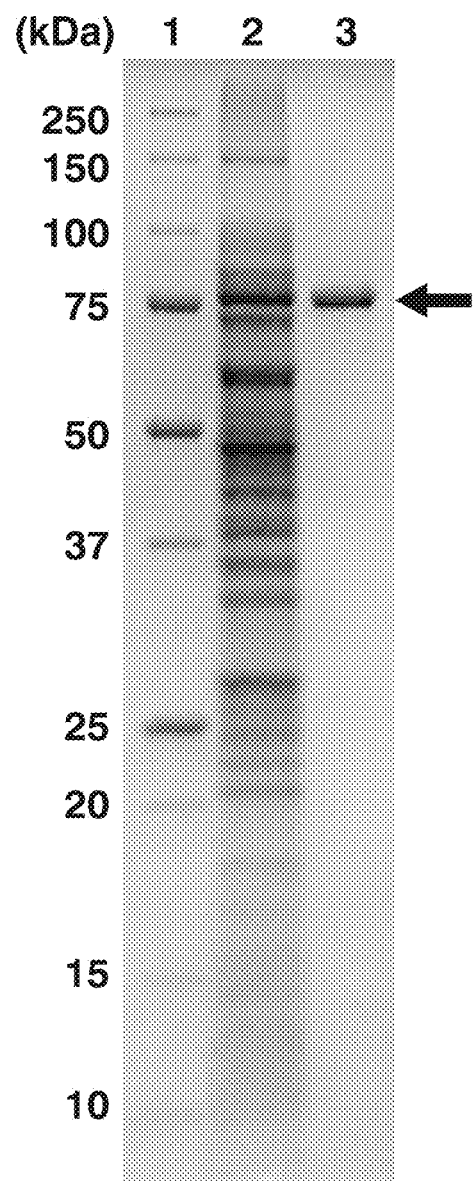
FIG. 4 is a diagram showing the SDS-PAGE analysis results of the OJ1M-273-1 protein obtained by expressing the OJ1M-273-1 gene in *E. coli* in Example 1.

Many microorganisms including filamentous fungi, bacteria and Archaea are difficult to culture, and it is said that about 99% of the microorganisms inhabiting microbial environments such as soil are still unknown. In particular, the culturing of microorganisms that exist in high-temperature environments is extremely difficult, and it is thought that only a mere 0.1% or less of the microorganisms that exist in soils have been able to be isolated and cultured with currently available microbial culturing techniques. This difficulty in culturing microorganisms from high-temperature soils is one of the reasons hindering the development of thermostable enzymes.

In recent years, as a result of the development of next generation giga sequencers that enable a large amount of sequencing of giga base pairs, whole genome sequencing of the microbial flora contained in soils or the like has become possible. By using this analysis technology, the metagenomic analysis method has been proposed, in which the genomic DNA of a microbial group is prepared from an environmental sample such as soil, the genomes of the group having non-uniform and miscellaneous genomic compositions are sequenced directly and comprehensively, and the sequenced data are assembled by a parallel computer, thereby reconstructing the genomic sequences of the microbial flora. This method has contributed to rapid progress in the genome sequencing of microorganisms that are difficult to culture.

As shown in Example 1 described below, the inventors of the present invention extracted the genomic DNA (metagenomic DNA) of microbial groups from collected high-temperature hot spring soils (for example, hot spring water of 58 to 78° C. containing soil, mud, biomat and biofilm and the like), and conducted shotgun sequencing and annotation of the metagenomic DNA, thus obtaining open reading frames (ORFs) encoding amino acid sequences similar to known β-glucosidase enzymes or β-xylosidase enzymes (namely, amino acid sequences having a sequence identity of 20% or greater, and having an expectation value (E-value) of less than $1e^{-20}$). Among the obtained ORFs, for each of the full-length ORFs for which a β-glucosidase catalytic domain or a β-xylosidase catalytic region was able to be confirmed, primers were designed based on the nucleotide sequence information of the ORF, and gene candidates were cloned from the metagenomic DNA of the high-temperature hot spring soil by the PCR method. The PCR-cloned DNAs were incorporated into *E. coli*, and proteins encoded by these nucleotide sequences were expressed and subjected to functional screening by PNPX degradation activity assay. Finally, a thermostable β-xylosidase (hereafter also referred to as "OJ1M-273-1" or "gene clone OJ1M-273-1") having PNPX degradation activity was obtained from these ORFs. The amino acid sequence of OJ1M-273-1 is represented by SEQ ID NO: 2, and the nucleotide sequence encoding the amino acid sequence of OJ1M-273-1 is represented by SEQ ID NO: 4.

As shown below in Example 1 described below, OJ1M-273-1 exhibits a high level of hydrolysis activity against PNPX, p-nitrophenyl-α-L-arabinofuranoside (hereafter sometimes abbreviated as PNPAF), and p-nitrophenyl-α-L-arabinopyranoside (hereafter sometimes abbreviated as PNPAP), and also exhibits high hydrolysis activity against arabinan and arabinogalactan. Further, OJ1M-273-1 also exhibits some hydrolysis activity against p-nitrophenyl-β-D-glucopyranoside (hereafter sometimes abbreviated as PNPG) and xylan. This substrate specificity suggests that OHM-273-1 is a glycoside hydrolase which has at least β-xylosidase activity, and which can also be used as an α-L-arabinofuranosidase and an α-L-arabinopyranosidase, meaning OHM-273-1 is potentially extremely useful as a multifunctional enzyme.

Moreover, the half life $T_{half}$ of the PNPX degradation activity of OJ1M-273-1 is about 180 minutes at both 90° C. and 95° C., and about 130 minutes at 100° C. In this manner, the β-xylosidase according to the present invention, including OJ1M-273-1, has excellent thermal stability, and is therefore ideal for hydrolysis processes of hemicellulose under high-temperature conditions.

In the present description, the expression "β-xylosidase activity" means enzymatic activity that promotes the hydrolysis of materials containing compounds having β-xylosidic bonds, and the value of that activity is represented by the hydrolysis activity against a PNPX substrate.

Further, in the present description, the expression "α-L-arabinofuranosidase activity" means enzymatic activity that promotes the hydrolysis of materials containing arabinofuranose residues, and the value of that activity is represented by the hydrolysis activity against a PNPAF substrate.

Furthermore, in the present description, the expression "α-L-arabinopyranosidase activity" means enzymatic activity that promotes the hydrolysis of materials containing arabinopyranose residues, and the value of that activity is represented by the hydrolysis activity against a PNPAP substrate.

Moreover, in the present description, the expression "has activity" means that the enzyme acts against at least one substrate, with a significant difference occurring in the amount of reducing ends or the color development reaction of the hydrolyzed substrate compared with a negative control.

Accordingly, the expression "has β-xylosidase activity" means that the enzyme acts at least against PNPX, and generates a significant difference in the amount of reducing ends or the color development reaction of the hydrolyzed substrate compared with a negative control.

The expression "has α-L-arabinofuranosidase activity" means that the enzyme acts at least against PNPAF, and generates a significant difference in the amount of reducing ends or the color development reaction of the hydrolyzed substrate compared with a negative control.

The expression "has α-L-arabinopyranosidase activity" means that the enzyme acts at least against PNPAP, and generates a significant difference in the amount of reducing ends or the color development reaction of the hydrolyzed substrate compared with a negative control.

When the amino acid sequence of OJ1M-273-1 was searched against a database of known amino acid sequences, the amino acid sequence that showed the highest sequence identity was that of a β-xylosidase (Genbank registration ID: WP_026140775.1) (SEQ ID NO: 9) belonging to the GH3 family of *Candidatus Caldatribacterium californiense*, and the sequence identity (homology) was 62% for the entire length, and 65% for the GH3 catalytic domain. From the substrate specificity and the sequence identity of the amino acid sequence with that of known proteins, it was clear that OJ1M-273-1 was a novel β-xylosidase belonging to the GH3 family.

OJ1M-273-1 has hydrolysis activity against a substrate of PNPX (namely, β-xylosidase activity) at least under conditions of 105° C. and pH 5.0. Actually, as shown below in Example 1, OJ1M-273-1 exhibits β-xylosidase activity within a broad temperature range from 70 to 110° C., and across a broad pH range from 4.5 to 7. More specifically, the β-xylosidase activity of OJ1M-273-1 increases with increasing temperature within a range from 70 to 105° C., but then tends to decrease rapidly above 105° C.

Generally, in a protein having some form of bioactivity, one or a plurality of amino acids can be deleted, substituted, or added, without impairing the bioactivity. In other words, in OJ1M-273-1, one or a plurality of amino acids can be deleted, substituted, or added without impairing the glycoside hydrolysis activity including the β-xylosidase activity.

Hence, the thermostable β-xylosidase according to the present invention is a thermostable glycoside hydrolase having a β-xylosidase catalytic domain including any of the following (A) to (C):

(A) a polypeptide including the amino acid sequence represented by SEQ ID NO: 1 or 2 (namely, the open reading frame OJ1M-273 or the gene clone OJ1M-273-1), (B) a polypeptide including an amino acid sequence in which at least one amino acid has been deleted, substituted, or added in the amino acid sequence represented by SEQ ID NO: 1 or 2, and having hydrolysis activity against a substrate of PNPX at least under conditions of 105° C. and pH 5.0, or (C) a polypeptide including an amino acid sequence having 75% or greater sequence identity with the amino acid sequence represented by SEQ ID NO: 1 or 2, and having hydrolysis activity against a substrate of PNPX at least under conditions of 105° C. and pH 5.0.

In the present description, a "polypeptide in which an amino acid is deleted" means a polypeptide in which a portion of the amino acids which constitute the polypeptide is missing (removed).

In the present description, a "polypeptide in which an amino acid is substituted" means a polypeptide in which an amino acid which constitutes the polypeptide has been replaced with a different amino acid.

In the present description, a "polypeptide in which an amino acid is added" means a polypeptide in which a new amino acid has been inserted within the polypeptide.

The amino acid sequence represented by SEQ ID NO: 1 is the amino acid sequence encoded by the open reading frame OJ1M-273 (SEQ ID NO: 1), which was isolated from a hot spring soil sample using the method described below in Example 1, and which, based on database analysis, was predicted as being an open reading frame of a β-glucosidase gene or a β-xylosidase gene.

In the aforementioned polypeptide of (B), the number of amino acids deleted, substituted, or added in the amino acid sequence represented by SEQ ID NO: 1 or 2 is preferably 1 to 20, more preferably 1 to 10, and still more preferably 1 to 5.

In the aforementioned polypeptide of (C), the sequence identity with the amino acid sequence represented by SEQ ID NO: 1 or 2 is not specifically limited as long as it is 75% or greater but less than 100%, but the sequence identity is preferably 80% or greater but less than 100%, more preferably 85% or greater but less than 100%, still more preferably 90% or greater but less than 100%, still more preferably 95% or greater but less than 100%, and most preferably 98% or greater but less than 100%.

The sequence identity (homology) between a pair of amino acid sequences is determined by juxtaposing the two amino acid sequences, while inserting gaps in some parts of the sequences to account for insertions and deletions, so as to achieve the best match between corresponding amino acids, and then calculating the proportion of matched amino acids relative to the whole amino acid sequences, excluding gaps, in the resulting alignment. The sequence identity between a pair of amino acid sequences can be determined using a variety of homology search software well known in the art. The sequence identity values between amino acid sequences in the present invention were obtained by calculation on the basis of an alignment obtained from the publicly known homology search software BLASTP.

The aforementioned polypeptides of (B) and (C) may be artificially designed, or may be homologs of OJ1M-273-1 or the like, or partial proteins thereof.

Each of the aforementioned polypeptides of (A) to (C) may be chemically synthesized based on the amino acid sequence, or may be generated by a protein expression system using the polynucleotide according to the present invention described below. Further, each of the polypeptides of (B) and (C) can also be artificially synthesized based on the polypeptide including the amino acid sequence represented by SEQ ID NO: 1 or 2, by using a gene recombination technique to introduce amino acid mutation(s).

Each of the polypeptides of (A) to (C) has hydrolysis activity (β-xylosidase activity) against a PNPX substrate at least under conditions of 105° C. and pH 5.0. As a result, a thermostable β-xylosidase can be obtained by having any of the polypeptides of (A) to (C) as the β-xylosidase catalytic domain.

The thermostable β-xylosidase according to the present invention uses PNPX as a substrate. The thermostable β-xylosidase may also use other β-glucans or oligosaccharides or the like besides PNPX as a substrate. Examples of substrates besides PNPX that can act as substrates for the thermostable β-xylosidase according to the present invention include PNPAF, PNPAP, PNPG, p-nitrophenyl-β-D-fucopyranoside (hereafter sometimes abbreviated as PNPbdFP), p-nitrophenyl-β-L-arabinopyranoside, p-nitrophenyl-β-D-mannopyranoside (hereafter sometimes abbreviated as PNPMP), p-nitrophenyl-α-D-galactopyranoside, p-nitrophenyl-β-D-galactopyranoside (hereafter sometimes abbreviated as PNPGA), p-nitrophenyl-α-L-fucopyranoside (hereafter sometimes abbreviated as PNPFP), p-nitrophenyl-α-L-rhamnopyranoside (hereafter sometimes abbreviated as PNPRP), and p-nitrophenyl-α-D-xylopyranoside (hereafter sometimes abbreviated as PNPadX); glucans having arabinose as a constituent sugar, such as arabinan and arabinogalactan; xylan; glucans composed of β-1,3 and β-1,4 linkages such as lichenan; crystalline celluloses such as Avicel, bacterial microcrystalline cellulose (hereafter sometimes abbreviated as BMCC) and filter paper; the non-crystalline cellulose known as phosphoric acid swollen Avicel (hereafter sometimes abbreviated as PSA); glucans composed of β-1,4 linkages such as CMC; oligosaccharides composed of β-1,4 linkages such as cellobiose; glucans composed of β-1,3 and β-1,6 linkages such as laminarin; glucans composed of β-1,3 linkages; glucans composed of β-1,6 linkages; and oligosaccharides composed of β-1,6 linkages such as gentiobiose. In addition to PNPX, the thermostable β-xylosidase according to the present invention preferably also acts against at least one substrate selected from the group consisting of PNPAF, PNPAP, PNPG, PNPbdFP, arabinan, arabinogalactan and xylan, more preferably acts against PNPX, PNPAF, PNPAP, arabinan, arabinogalactan, PNPG and xylan, and still more preferably acts against PNPX, PNPAF, PNPAP, arabinan and arabinogalactan.

The thermostable β-xylosidase according to the present invention exhibits hydrolysis activity (β-xylosidase activity) against a PNPX substrate, at least under conditions of pH 5.0, preferably within a temperature range from 90 to 110° C., more preferably within a temperature range from 80 to 110° C., and still more preferably within a temperature range from 70 to 110° C. The optimum temperature of the thermostable β-xylosidase according to the present invention is preferably within a range from 90 to 110° C., and more preferably within a range from 100 to 110° C.

The term "thermostable" used in relation to the thermostable β-xylosidase according to the present invention means the β-xylosidase exhibits β-xylosidase activity within a temperature range from 70 to 110° C.

The optimum pH of the thermostable β-xylosidase according to the present invention is within a range from pH 4.5 to 6.0. The thermostable β-xylosidase according to the present invention preferably exhibits β-xylosidase activity at least within a range from pH 4.5 to 7.0.

The thermostable β-xylosidase according to the present invention may also have, in addition to the β-xylosidase activity, other glycoside hydrolase activity besides the β-xylosidase activity. Examples of this other glycoside hydrolase activity include α-L-arabinofuranosidase activity, α-L-arabinopyranosidase activity, endoglucanase activity, xylanase activity, β-glucosidase activity or cellobiohydrolase activity. The thermostable β-xylosidase according to the present invention preferably has at least one activity selected from the group consisting of α-L-arabinofuranosidase activity and α-L-arabinopyranosidase activity in addition to the β-xylosidase activity, and more preferably has all of β-xylosidase activity, α-L-arabinofuranosidase activity and α-L-arabinopyranosidase activity.

The thermostable β-xylosidase according to the present invention may be an enzyme composed solely of the β-xylosidase catalytic domain including any of the aforementioned polypeptides of (A) to (C), or may also include other domains in addition to the β-xylosidase catalytic domain. Examples of these other domains include other domains of conventionally known β-xylosidases besides the enzyme catalytic domain. For example, the thermostable β-xylosidase according to the present invention also includes enzymes obtained by substituting the enzyme catalytic domain in a publicly known β-xylosidase with any of the aforementioned polypeptides of (A) to (C).

When the thermostable β-xylosidase according to the present invention includes one or more other domains besides the β-xylosidase catalytic domain, the thermostable β-xylosidase preferably includes a Fibronectin type III domain.

The Fibronectin type III domain may be positioned upstream (on the N-terminal side) or downstream (on the C-terminal side) from the β-xylosidase catalytic domain. Further, the Fibronectin type III domain and the β-xylosidase catalytic domain may be bonded either directly or via a linker region of appropriate length. In the thermostable β-xylosidase according to the present invention, a Fibronectin type III domain preferably exists either upstream or downstream from the β-xylosidase catalytic domain with a linker region positioned therebetween, and a thermostable β-xylosidase in which a Fibronectin type III domain exists downstream from the β-xylosidase catalytic domain with a linker region positioned therebetween is particularly preferred.

The thermostable β-xylosidase according to the present invention may also have, at either the N-terminal or the C-terminal, a signal peptide capable of migration to and localization within a specific region within a cell, or a signal peptide that causes secretion from a cell. Examples of these types of signal peptides include apoplastic transport signal peptides, endoplasmic reticulum retention signal peptides, nuclear transport signal peptides, and secretory signal peptides. Specific examples of the endoplasmic reticulum retention signal peptides include signal peptides including an HDEL amino acid sequence. In those cases when the thermostable β-xylosidase according to the present invention has a signal peptide at the N-terminal or the C-terminal, the thermostable β-xylosidase expressed in a transformant can be secreted from the cell or localized within the endoplasmic reticulum or the like of the cells.

Furthermore, the thermostable β-xylosidase according to the present invention may also have various types of tags added, for example at the N-terminal or the C-terminal of the thermostable β-xylosidase, so as to facilitate easy purification in the case of generation using an expression system. Examples of tags that may be used include the types of tags widely used in the expression or purification of recombinant proteins, such as His tags, HA (hemagglutinin) tags, Myc tags and Flag tags.

In other words, one aspect of the thermostable β-xylosidase according to the present invention contains a β-xylosidase catalytic domain including any of the aforementioned polypeptides of (A) to (C); and also contains, according to need, at least one moiety selected from the group consisting of a Fibronectin type III domain positioned on either the upstream side or the downstream side of the β-xylosidase catalytic domain, a linker region, a signal peptide added to either the N-terminal or the C-terminal of the thermostable β-xylosidase, a tag added to either the N-terminal or the C-terminal of the thermostable β-xylosidase, and a cellulose-binding module.

[Polynucleotide Encoding Thermostable β-Xylosidase]

The polynucleotide according to the present invention encodes the thermostable β-xylosidase according to the present invention. By introducing an expression vector incorporating the polynucleotide into a host, the thermostable β-xylosidase can be generated by using the expression system of the host.

Specifically, the polynucleotide according to the present invention is a polynucleotide having a region encoding a β-xylosidase catalytic domain, the region including any of the following nucleotide sequences (a) to (e):

(a) a nucleotide sequence encoding a polypeptide including the amino acid sequence represented by SEQ ID NO: 1 or 2, (b) a nucleotide sequence encoding a polypeptide which includes an amino acid sequence in which at least one amino acid has been deleted, substituted, or added in the amino acid sequence represented by SEQ ID NO: 1 or 2, and has hydrolysis activity against a substrate of PNPX at least under conditions of 105° C. and pH 5.0, (c) a nucleotide sequence encoding a polypeptide which includes an amino acid sequence having 75% or greater sequence identity with the amino acid sequence represented by SEQ ID NO: 1 or 2, and has hydrolysis activity against a substrate of PNPX at least under conditions of 105° C. and pH 5.0, (d) a nucleotide sequence, having 80% or greater sequence identity with a nucleotide sequence represented by SEQ ID NO: 3 or 4, and encoding a polypeptide that has hydrolysis activity against a substrate of PNPX at least under conditions of 105° C. and pH 5.0, or (e) a nucleotide sequence of a polynucleotide which hybridizes under stringent conditions with a polynucleotide including the nucleotide sequence represented by SEQ ID NO: 3 or 4, the nucleotide sequence encoding a polypeptide having hydrolysis activity against a substrate of PNPX at least under conditions of 105° C. and pH 5.0.

In the present description, a "polynucleotide in which a nucleotide is deleted" means a polynucleotide in which a portion of the nucleotides which constitute the polynucleotide is missing (removed).

In the present description, a "polynucleotide in which a nucleotide is substituted" means a polynucleotide in which a nucleotide which constitutes the polynucleotide has been replaced with a different nucleotide.

In the present description, a "polynucleotide in which a nucleotide is added" means a polynucleotide in which a new nucleotide has been inserted within the polynucleotide.

In the present description, the expression "stringent conditions" can be exemplified by the method disclosed in Molecular Cloning: A Laboratory Manual, Third Edition (Sambrook et al., Cold Spring Harbor Laboratory Press). This example includes conditions in which hybridization is performed by incubation in a hybridization buffer composed of 6×SSC (composition of 20×SSC: 3 M sodium chloride, 0.3 M citric acid solution, pH 7.0), 5×Denhardt's solution (composition of 100×Denhardt's solution: 2% by mass of bovine serum albumin, 2% by mass of Ficoll, 2% by mass of polyvinylpyrrolidone), 0.5% by mass of SDS, 0.1 mg/mL of salmon sperm DNA, and 50% formamide, at a temperature of 42 to 70° C. for several hours to overnight. The washing buffer used in the washing performed after the incubation is preferably 1×SSC solution containing 0.1% by mass of SDS, and is more preferably 0.1×SSC solution containing 0.1% by mass of SDS.

In the aforementioned nucleotide sequences of (a) to (e), it is preferable to select a degenerate codon having a high frequency of usage in the host. For example, the aforementioned nucleotide sequence of (a) may be either the nucleotide sequence represented by SEQ ID NO: 3, the nucleotide sequence represented by SEQ ID NO: 4, or a nucleotide sequence obtained by modifying the nucleotide sequence represented by SEQ ID NO: 3 or 4 to codons having a higher frequency of usage in the host without changing the amino acid sequence encoded by the nucleotide sequence. This modification of codons can be achieved using a known gene sequence variation technique or artificial gene synthesis.

The polynucleotide including the nucleotide sequence represented by SEQ ID NO: 3 or 4 may be chemically synthesized based on the nucleotide sequence information, or may be obtained from the natural world using gene recombination techniques as either a full length gene that encodes OJ1M-273-1 (hereafter sometimes referred to as the "OJ1M-273-1 gene") or a partial region thereof including the β-xylosidase catalytic domain. The full length of the OJ1M-273-1 gene or the partial region thereof can be obtained, for example, by collecting a sample containing microorganisms from the natural world, and conducting PCR using a genomic DNA recovered from the sample as a template, with a forward primer and a reverse primer designed by normal methods based on the nucleotide sequence represented by SEQ ID NO: 3 or 4. The cDNA synthesized by a reverse transcription reaction using mRNA recovered from the sample as a template may also be used as a template.

The sample from which the nucleic acid used as a template is recovered is preferably a sample collected from a high-temperature environment such as a hot spring soil.

In the aforementioned nucleotide sequence of (d), the sequence identity with the nucleotide sequence represented by SEQ ID NO: 3 or 4 is not specifically limited as long as it is 80% or greater but less than 100%, but the sequence identity is preferably 85% or greater but less than 100%, more preferably 90% or greater but less than 100%, and still more preferably 95% or greater but less than 100%.

The sequence identity (homology) between a pair of nucleotide sequences is determined by juxtaposing the two nucleotide sequences, while inserting gaps in some parts of the sequences to account for insertions and deletions, so as to achieve the best match between corresponding nucleotides, and then calculating the proportion of matched nucleotides relative to the whole nucleotide sequences, excluding gaps, in the resulting alignment. The sequence identity between a pair of nucleotide sequences can be determined using a variety of homology search software well known in the art. The sequence identity values between nucleotide sequences in the present invention were obtained by calculation on the basis of an alignment obtained from the publicly known homology search software BLASTN.

For example, each of the polynucleotides including an aforementioned nucleotide sequence of (b), (c) or (d) can be artificially synthesized by deleting, substituting, or adding one or a plurality of nucleotides in a polynucleotide including the nucleotide sequence represented by SEQ ID NO: 3 or 4.

Further, the nucleotide sequence of (b), (c) or (d) may also be a full length sequence of a homologous gene of the OJ1M-273-1 gene or a partial sequence thereof. The homologous gene of the OJ1M-273-1 gene can be obtained by a gene recombination technique used in obtaining homologous genes of a gene for which the nucleotide sequence is already known.

The polynucleotide according to the present invention may have only the region encoding the β-xylosidase catalytic domain, or may also have, in addition to this region, one or more other regions encoding a cellulose-binding module, a linker sequence, various types of signal peptides, or various types of tags or the like.

In other words, one aspect of the polynucleotide according to the present invention contains a region encoding a β-xylosidase catalytic domain, the region including one of the aforementioned nucleotide sequences of (a) to (e), and also contains, according to need, a region encoding at least one moiety selected from the group consisting of a Fibronectin type III domain, a cellulose-binding module, a linker region, a signal peptide and a tag.

[Expression Vector]

The expression vector according to the present invention incorporates the aforementioned polynucleotide according to the present invention, and is capable of expressing, in a host cell, a polypeptide having hydrolysis activity against a PNPX substrate at least under conditions of 105° C. and pH 5.0. In other words, the expression vector of the present invention is an expression vector into which the polynucleotide according to the present invention has been incorporated in a state capable of expressing the thermostable β-xylosidase according to the present invention. More specifically, an expression cassette composed, in order from the upstream side, of DNA having a promoter sequence, the aforementioned polynucleotide according to the present invention and DNA having a terminator sequence, must be incorporated into the expression vector. Incorporation of the polynucleotide into the expression vector can be achieved using known gene recombination techniques. A commercially available expression vector preparation kit may also be used to achieve incorporation of the polynucleotide into the expression vector.

In the present description, an "expression vector" is a vector including, in order from the upstream side, DNA having a promoter sequence, DNA having a sequence for incorporating foreign DNA, and DNA having a terminator sequence.

The aforementioned expression vector may be a vector for introduction into a prokaryotic cell such as E. coli, or a vector for introduction into a eukaryotic cell such as a yeast, a filamentous fungus, an insect cultured cell, a mammalian cultured cell, or a plant cell. Any arbitrary widely used expression vector can be selected and used in accordance with the respective host.

The expression vector according to the present invention is preferably an expression vector into which not only the aforementioned polynucleotide according to the present invention, but also a drug resistance gene or the like, has been incorporated. This facilitates the screening of host cells transformed by the expression vector and non-transformed host cells.

Examples of the drug resistance gene include a kanamycin resistance gene, a hygromycin resistance gene and a bialaphos resistance gene.

[Transformant]

The transformant according to the present invention is a transformant into which the expression vector according to the present invention has been introduced. In this transformant, the thermostable β-xylosidase according to the present invention can be expressed. The host into which the expression vector is introduced may be a prokaryotic cell such as E. coli, or a eukaryotic cell such as a yeast, a filamentous fungus, an insect cultured cell, a mammalian cultured cell, or a plant cell. In other words, examples of the transformant according to the present invention include E. coli, a yeast, a filamentous fungus, an insect cultured cell, a mammalian cultured cell or a plant cell into which the expression vector according to the present invention has been introduced.

By culturing a transformant of E. coli, the thermostable β-xylosidase according to the present invention can be generated more easily and in large amounts. On the other hand, because proteins are glycosylated in eukaryotic cells, by using a transformant of a eukaryotic cell, a thermostable β-xylosidase can be generated which exhibits superior thermal stability to that achieved by using a transformant of a prokaryotic cell.

There are no particular limitations on the method used for producing the transformant using the expression vector, and the types of methods typically used in the production of transformants can be employed. Examples of methods that can be used include a heat shock method, an Agrobacterium method, a particle gun method, an electroporation method, and a PEG (polyethylene glycol) method. Of these, if the host is a plant cell, a particle gun method or an Agrobacterium method is preferred.

When a prokaryotic cell, a yeast, a filamentous fungus, an insect cultured cell, or a mammalian cultured cell or the like is used as the host, the obtained transformant can generally be cultured by a conventional method in a similar manner to that of the non-transformed host.

[Method for Producing Thermostable β-Xylosidase]

The method for producing a thermostable β-xylosidase according to the present invention is a method for generating a thermostable β-xylosidase in the aforementioned transformant according to the present invention. By culturing a transformant that has been produced using an expression vector into which the aforementioned polynucleotide according to the present invention has been incorporated downstream from a promoter having no ability to regulate the timing or the like of the expression, the thermostable β-xylosidase according to the present invention can be expressed constitutively within the transformant. On the other hand, in the case of a transformant produced using a so-called expression inducible promoter to induce the expression by means of a specific compound or temperature condition or the like, the thermostable β-xylosidase according to the present invention can be expressed in the transformant by culturing the transformant and conducting an induction treatment suitable for the respective expression-inducing condition.

The thermostable β-xylosidase generated by the transformant may be used in a state where it is retained inside the transformant, or may be extracted from the transformant and purified.

The method used for extracting and purifying the thermostable β-xylosidase from the transformant is not particularly limited, as long as the method does not impair the activity of the thermostable β-xylosidase, and extraction can be carried out by methods commonly used for extracting polypeptides from cells or biological tissue. Examples of the method include a method in which the transformant is immersed in an appropriate extraction buffer to extract the thermostable β-xylosidase, and the resulting liquid extract and the solid residue are then separated. The extraction buffer preferably contains a solubilizing agent such as a surfactant. If the transformant is a plant, then the transformant may be shredded or crushed prior to immersion in the extraction buffer. Further, in terms of the method used for separating the liquid extract and the solid residue, known solid-liquid separation treatments such as a filtration method, pressurized filtration method or centrifugation treatment may be used, or the extraction buffer containing the immersed transformant may be squeezed. The thermostable β-xylosidase in the liquid extract can be purified by known purification methods such as a salting-out method, ultrafiltration method, or chromatography method.

If the thermostable β-xylosidase according to the present invention is expressed in the transformant in a state having a secretory signal peptide, then a solution containing the thermostable β-xylosidase can be readily obtained by culturing the transformant and then collecting the culture liquid supernatant obtained by removal of the transformant from the obtained culture. Further, if the thermostable β-xylosidase according to the present invention has a tag such as an His tag, then the thermostable β-xylosidase in the liquid extract or in the culture supernatant can be easily purified by an affinity chromatography method using the tag.

In other words, the method for producing a thermostable β-xylosidase according to the present invention includes generating the thermostable β-xylosidase within the transformant according to the present invention, and also includes, according to need, extracting the thermostable β-xylosidase from the transformant and purifying the thermostable β-xylosidase.

[Glycoside Hydrolase Mixture]

The glycoside hydrolase mixture according to the present invention includes the aforementioned thermostable β-xylosidase according to the present invention or a thermostable β-xylosidase produced by the method for producing a thermostable β-xylosidase according to the present invention, and at least one other glycoside hydrolase. The thermostable β-xylosidase produced by the aforementioned method for producing a thermostable β-xylosidase according to the present invention may be in a state where it is incorporated inside the transformant, or may be extracted from the transformant and purified. By using the thermostable β-xylosidase according to the present invention as a mixture with one or more other glycoside hydrolases in a polysaccharide hydrolysis reaction, materials composed of lignocellulose containing persistent cellulose, hemicellulose and lignin can be degraded more efficiently.

There are no particular limitations on the other glycoside hydrolase besides the aforementioned thermostable β-xylosidase included in the glycoside hydrolase mixture, as long as it exhibits lignocellulose hydrolysis activity. Examples of the other glycoside hydrolase besides the aforementioned thermostable β-xylosidase included in the glycoside hydrolase mixture include hemicellulases such as xylanases, as well as cellobiohydrolases, β-glucosidases and endoglucanases. The glycoside hydrolase mixture according to the present invention is preferably a mixture containing at least one glycoside hydrolase from among hemicellulases and endoglucanases in addition to the aforementioned thermostable β-xylosidase, and is more preferably a mixture containing both a hemicellulase and an endoglucanase in addition to the aforementioned thermostable β-xylosidase. Among the various possibilities, the glycoside hydrolase mixture according to the present invention is preferably a mixture containing at least one glycoside hydrolase selected from the group consisting of xylanases, β-xylosidases, cellobiohydrolases and endoglucanases in addition to the aforementioned thermostable β-xylosidase, and is more preferably a mixture containing all of a xylanase, a β-xylosidase, a cellobiohydrolase and an endoglucanase in addition to the thermostable β-xylosidase.

The other glycoside hydrolase included in the glycoside hydrolase mixture besides the aforementioned thermostable β-xylosidase is preferably a thermostable glycoside hydrolase having glycoside hydrolase activity at least at 85° C., and is more preferably a thermostable glycoside hydrolase having glycoside hydrolase activity at 70 to 90° C. By ensuring that all of the enzymes contained in the glycoside hydrolase mixture are thermostable (that is, have an optimum temperature for the enzymatic activity or a melting temperature for the enzyme protein of 70° C. or higher), the hydrolysis reaction of materials containing lignocellulose by the glycoside hydrolase mixture can be conducted efficiently under high-temperature conditions. In other words, if the glycoside hydrolase mixture contains only thermostable glycoside hydrolases, then by using the glycoside hydrolase mixture in a hydrolysis treatment of a material containing lignocellulose, it becomes possible to conduct a hydrolysis reaction of the above material in a high-temperature environment in which the hydrolysis temperature is from 70 to 90° C. (namely, a high-temperature hydrolysis). With this high-temperature hydrolysis, the amount of enzymes and the time required for the hydrolysis can be reduced markedly, and the hydrolysis costs can be cut dramatically.

[Method for Producing Lignocellulose Degradation Product]

The method for producing a lignocellulose degradation product according to the present invention is a method for obtaining a lignocellulose degradation product (for example, a degradation product containing monosaccharides such as glucose, xylose or arabinose), the method including hydrolyzing oligosaccharides, either generated by hydrolysis of hemicellulose by a xylanase or generated by hydrolysis of cellulose by a cellobiohydrolase, with the thermostable β-xylosidase according to the present invention, thereby producing monosaccharides.

More specifically, the method for producing a lignocellulose degradation product is a method of producing a degradation product of a material containing lignocellulose, the degradation product containing a degradation product of hemicellulose, a degradation product of cellulose, or both a degradation product of hemicellulose and a degradation product of cellulose, by bringing a material containing the lignocellulose, such as a material containing lignocellulose that includes at least one compound selected from the group consisting of cellulose and hemicellulose, into contact with the thermostable β-xylosidase according to the present invention, the transformant according to the present invention, a thermostable β-xylosidase produced using the method for producing a thermostable β-xylosidase according to the present invention, or the glycoside hydrolase mixture according to the present invention.

There are no particular limitations on the material containing lignocellulose provided the material contains at least hemicellulose or cellulose. Specific examples of such materials include cellulosic biomass such as weeds and agricultural waste materials, or used paper or the like. The material is preferably subjected to a mechanical treatment such as crushing or shredding, a chemical treatment with acid or alkali or the like, or a treatment such as immersion or dissolution in an appropriate buffer, prior to being brought into contact with the thermostable β-xylosidase according to the present invention.

In other words, the method for producing a lignocellulose degradation product according to the present invention may also include a step in which the material containing lignocellulose is treated mechanically, treated chemically, or treated by immersion or dissolution in a buffer, prior to being brought into contact with the thermostable β-xylosidase according to the present invention.

The reaction conditions for the hydrolysis reaction of hemicellulose by the thermostable β-xylosidase according to the present invention may be any conditions under which the thermostable β-xylosidase exhibits cellooligosaccharide hydrolysis activity. For example, the reaction is preferably conducted at a temperature of 70 to 110° C. and a pH of 4.5 to 7.0, more preferably conducted at a temperature of 90 to 110° C. and a pH of 4.5 to 6.5, and still more preferably conducted at a temperature of 95 to 110° C. and a pH of 4.5 to 6.0. The reaction time for the hydrolysis reaction may be adjusted appropriately with due consideration of the type, the method of pretreatment, and the amount and the like of the material supplied to the hydrolysis reaction. For example, the hydrolysis reaction may be performed for a reaction time of 10 minutes to 100 hours, but in the case of degradation of a material containing a cellulosic biomass, the hydrolysis reaction is typically performed for a reaction time of 1 to 100 hours.

In the hydrolysis reaction of the material containing lignocellulose, it is also preferable to use at least one other type of glycoside hydrolase in addition to the thermostable β-xylosidase according to the present invention. This other glycoside hydrolase may be similar to the glycoside hydrolases mentioned above for inclusion in the aforementioned glycoside hydrolase mixture, and is preferably a thermostable glycoside hydrolase having glycoside hydrolase activity at least at 85° C., and preferably at least at temperatures of 70 to 90° C., more preferably at temperatures of 70 to 105° C., and still more preferably at temperatures of 70 to 110° C. Further, one aspect of the aforementioned method for producing a lignocellulose degradation product uses the thermostable β-xylosidase according to the present invention, the transformant according to the present invention, or a thermostable β-xylosidase produced by the method for producing a thermostable β-xylosidase according to the present invention, whereas another aspect of the method uses the aforementioned glycoside hydrolase mixture.

EXAMPLES

Next, the present invention is described in further detail based on a series of examples, but the present invention is in no way limited by the following examples.

Example 1

Cloning of Novel Thermostable β-Xylosidase from Hot Spring Soil

<1> DNA Extraction from Hot Spring Soil and Whole Genome Sequencing (WGS)

With the purpose of searching for genes of novel thermostable β-xylosidases which exhibit activity at 70 to 110° C., soil DNA was collected from neutral to weakly alkaline hot springs, and nucleotide sequencing was conducted of the metagenomic DNA of the microbial flora contained in the soils.

The soil samples from neutral to weakly alkaline hot springs were obtained by collecting hot spring water containing soil, mud and biomat from five sampling points (metagenomic DNA samples N2, AR19, AR15, OJ1 and H1) at 3 locations in Japan having gushing high-temperature outdoor hot springs. These hot spring soil samples each had a temperature within a range from 58 to 78° C. and a pH within a range from 7.2 to 8 at the time of collection.

DNA was extracted from 10 g of each of the collected hot spring soil samples by using a DNA extraction kit (ISOIL Large for Beads ver. 2, manufactured by Nippon Gene Co., Ltd.). The extracted DNA was subjected to shotgun sequencing of the metagenomic DNA using a sequencer GS FLX Titanium 454 manufactured by Roche Diagnostics Ltd., and a sequencer GA2x manufactured by Illumina, Inc. Five μg of the extracted DNA was used in the 454 sequencer, whereas in the GA2x sequencer, an amplified product prepared using a genome DNA amplification kit (GenomiPhi V2 DNA Amplification Kit, manufactured by GE Healthcare, Inc.) was used to perform the metagenomic DNA sequencing. In the case of sequencing using the GA2x, the DNA library and the reagent were introduced into the flow cell using a cBot manufactured by Illumina, Inc., and from a single DNA molecule, a cluster having the same sequence was formed automatically within the flow cell. Using the GA2x, 101 bp paired end sequencing was performed, thus obtaining the metagenomic sequence data.

Metagenomic DNA sequencing of the hot spring soil sample OJ1 (hereafter sometimes referred to as the OJ1 metagenome) in the 454 sequencer yielded an average read length of 390 bp, a total read number of 6,301,450, and a total quantity of sequenced genomes of 2,456,206,434 bp, and sequencing in the GA2x sequencer yielded an average read length of 114 bp paired ends, a total read number of 545,185,016, and a total quantity of sequenced genomes of 62/151,091,824 bp, meaning a whole genome sequence (WGS) data set totaling 64.6 Gbp was obtained.

<2> Assembly and Statistics of Hot Spring Metagenomic Data

For the nucleotide sequences read by the 454 sequencer and the GA2x sequencer, CLC Genomics Workbench (ver. 5.4.8) from CLC bio A/S was used to perform quality filtering and de novo assembly. Following quality filtering, the total read length of the reads obtained from the 454 sequencer was 2,446,280,452 bp, and the total read length of the nucleotide sequence data obtained from the GA2x sequencer was 54,066,191,005 bp. Following assembly, the number of contigs having a length of 500 bp or longer was 2,080,555, the total length was 1,083,520,858 bp, and the maximum contig length was 1,063,869 bp.

<3> Prediction of Open Reading Frames (ORFS) of β-Xylosidase

Sequences having EC numbers of 3.2.1.4 (cellulase), 3.2.1.21 (β-glucosidase), 3.2.1.37 (β-xylosidase), 3.2.1.91 (cellulose 1,4-β-cellobiosidase) and 3.2.1.8 (endo-1,4-β-xylanase) were downloaded (date of access: 2011/12/9) from the UniProt database (http://www.uniprot.org/), and a proteome local database of these glycoside hydrolase genes was constructed. Using the annotation software Metagene (Noguchi et al., DNA Research, 2008, 15(6)), gene regions (=open reading frames) were predicted from the contig sequences obtained in section <2> above (Metagene option: −m). In order to extract the glycoside hydrolase genes from the predicted ORFs, reference was made to the local database using BLASTP (blastall ver. 2.2.18). Furthermore, the option conditions for BLASTP were set such that: "Filter query sequence=false", "Expectation value (E)<1e$^{-20}$" (hereafter, default values were set such that: "Cost to open a gap=−1", "Cost to extended gap=−1", "X dropoff value for gapped alignment=0", "Threshold for extending hits=0", and "Word size=default"), and the hit ORF sequences were collected as glycoside hydrolase genes. The collected nucleotide sequences included various glycoside hydrolase genes such as cellulases, endohemicellulases and debranching enzymes.

<4> Glycoside Hydrolase (GH) Family Classification of Genes

Functional classification of the nucleotide sequences collected in section <3> above was performed with reference to the protein functional domain sequence database Pfam HMMs (Pfam version 23.0 and HMMER v2.3; Finn et al., Nucleic Acids Research Database, 2010, Issue 38, pp. D211 to 222). Specifically, the glycoside hydrolase (GH) family of each of the nucleotide sequences collected in section <3> above was determined on the basis of homology with the Pfam domain database by using the protein motif search program HMMER (Durbin et al., "The theory behind profile HMMs. Biological sequence analysis: probabilistic models of proteins and nucleic acids", 1998, Cambridge University Press; hmmpfam (Ver. 2.3.2), E-value cutoff <1e$^{-5}$; Database=Pfam_fs (models that can be used to find fragments of the represented domains in a sequence)). Nucleotide sequences which covered 70% or more of the GH catalytic domain sequence were counted as enzyme genes belonging to that particular family.

Based on the BLASTP homology search and the HMMER domain search using the metagenome OJ1 sequence data, 478 ORFs (331 full-length ORFs and 147 partial length ORFs) were predicted as β-glucosidase or β-xylosidase genes.

The GH family classification results of these ORFs are shown in Table 1. ORFs for which the coverage of the GH catalytic domain sequence was 70% or greater were classified into each of the GH families. As shown in Table 1, from the OJ1 metagenome, 46 full-length ORFs belonging to the GH family 1, 197 full-length ORFs belonging to the GH family 3, 1 full-length ORF belonging to the GH family 16, 1 full-length ORF belonging to the GH family 26, 37 full-length ORFs belonging to the GH family 31, 1 full-length ORF belonging to the GH family 39, 47 full-length ORFs belonging to the GH family 43, and 1 full-length ORF belonging to the GH family 52 were obtained.

TABLE 1

| | GH family classification of β-glucosidase genes or β-xylosidase genes | | | | | | | | |
|---|---|---|---|---|---|---|---|---|---|
| OJ1 Metagenome | GH1 | GH3 | GH16 | GH26 | GH31 | GH39 | GH43 | GH52 | total |
| Full-length ORFs | 46 | 197 | 1 | 1 | 37 | 1 | 47 | 1 | 331 |
| Partial length ORFs | 4 | 118 | 0 | 0 | 11 | 0 | 14 | 0 | 147 |
| Total number of ORFs | 50 | 315 | 1 | 1 | 48 | 1 | 61 | 1 | 478 |

<5> Gene Cloning from Open Reading Frame OJ1M-273

Primers were designed for all of the ORFs that were predicted as β-glucosidase genes or β-xylosidase genes, and the genes were amplified from the hot spring soil metagenomic DNA by PCR. The amplified PCR product was inserted into a pET101/D-TOPO vector of a Champion pET Directional TOPO Expression Kit (manufactured by Life Technologies Inc.), and transformed into a One Shot TOP10 strain. Positive clones were selected by colony PCR and cultured in an LB liquid medium containing 100 mg/L of ampicillin at a temperature of 37° C. and 200 rpm for 17 to 20 hours, and then plasmids were prepared using a miniprep kit (Wizard plus SV Minipreps DNA Purification System, manufactured by Promega Corporation). Sequence confirmation of the prepared plasmids was performed using a 3730 DNA Analyzer sequencer manufactured by Life Technologies Corporation.

Four gene clones OJ1M-273-1, OJ1M-273-3, OJ1M-273-12 and OJ1M-273-18 were obtained by PCR cloning from the open reading frame OJ1M-273 (SEQ ID NO: 3) that was predicted as an open reading frame of a β-glucosidase gene or a β-xylosidase gene. The nucleotide sequence (SEQ ID NO: 3) of the open reading frame OJ1M-273 was 2,178 bp, but because the paired end sequence of the GA2x sequencer was used, the sequence included unknown sequences ("n" in SEQ ID NO: 3, and "Xaa" in SEQ ID NO: 1), and the nucleotide sequence (SEQ ID NO: 4) of the actually obtained β-xylosidase candidate gene OJ1M-273-1 was 2,247 bp.

Figure 1A:
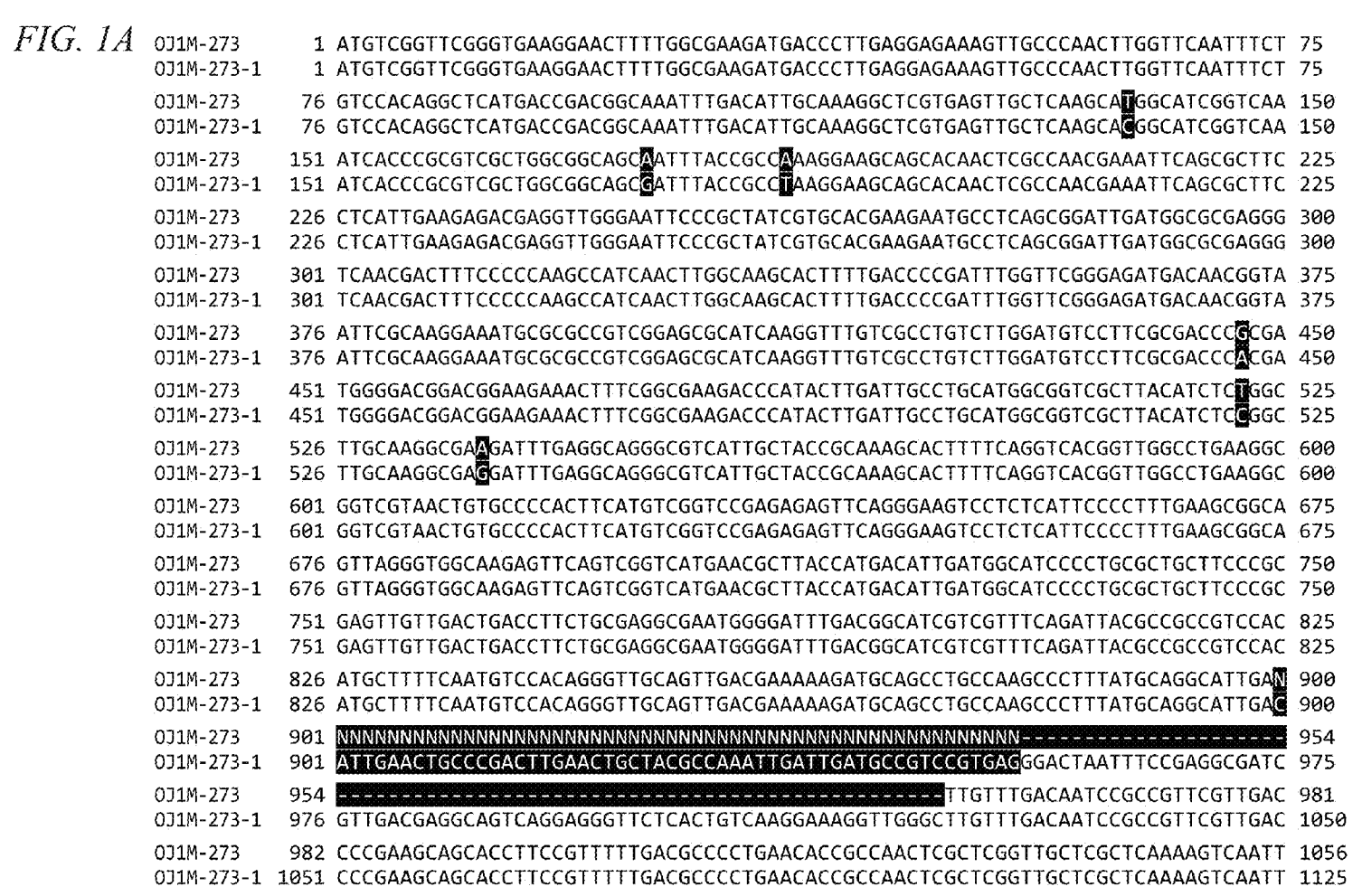

FIG. 1A and FIG. 1B show the alignment of the nucleotide sequences of the open reading frame OJ1M-273 (SEQ ID NO: 3) and the β-xylosidase candidate gene 0.1M-273-1 (SEQ ID NO: 4). FIG. 2 shows the alignment of the amino acid sequence (SEQ ID NO: 1) of the open reading frame OJ1M-273 and the amino acid sequence (SEQ ID NO: 2) of the β-xylosidase candidate gene OJ1M-273-1. In each of the figures, white on black text indicates those sequence portions where the nucleotides or amino acids differ, or sequence portions that are unknown in the open reading frame.

The β-xylosidase candidate gene OJ1M-273-1 encoded a polypeptide (SEQ ID NO: 2) containing 748 amino acid residues and was a full-length sequence (SEQ ID NO: 4), wherein the polypeptide started from a methionine as the amino acid residue at position 1, and the 3' end of the nucleotide sequence encoding the polypeptide ended with a termination codon. Based on the sequence homology of the motif, it was predicted that the 406 amino acids from the methionine (M) at position 12 through to the leucine (L) at position 417 encoded by the β-xylosidase candidate gene OJ1M-273-1 represented a catalytic domain of the glycoside hydrolase family 3. According to analysis using the signal sequence prediction software SignalP 4.1, the amino acid sequence encoded by the β-xylosidase candidate gene OJ1M-273-1 was not predicted to contain a signal peptide. The gene clone was a novel sequence for which the amino acid sequence encoded by the gene clone exhibited 65% and 62% amino acid sequence identity with the GH3 catalytic domain and the full length sequence respectively of the β-xylosidase of *Candidatus Caldatribacterium californiense* (Genbank registration ID: WP_026140775.1) (SEQ ID NO: 9). The sequence homology values were calculated using the ClustalW algorithm.

Figure 3:
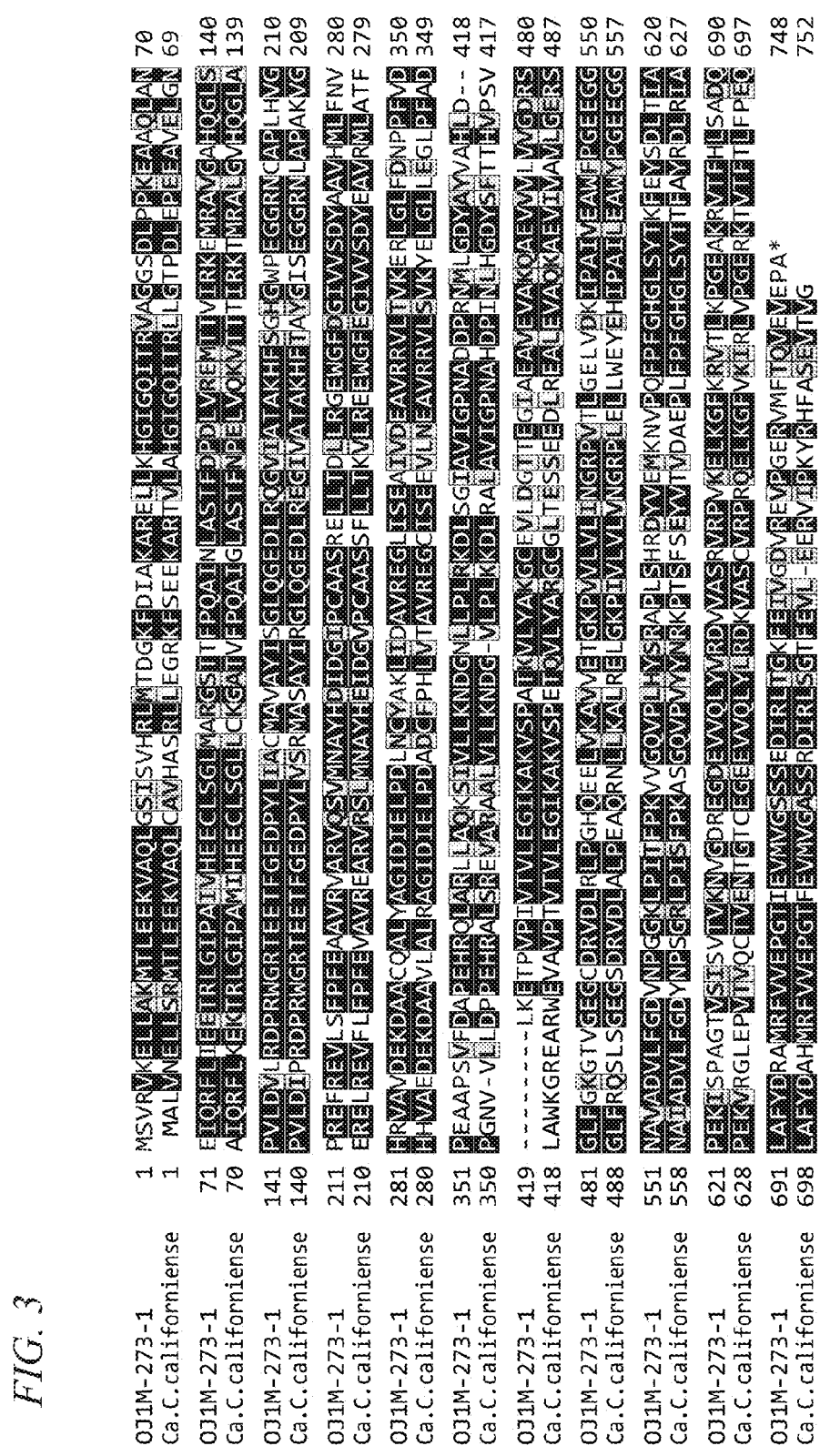

FIG. 3 shows the alignment of the amino acid sequence (SEQ ID NO: 2) of the β-xylosidase candidate gene OJ1-273-1 and the amino acid sequence (SEQ ID NO: 9) of the β-xylosidase of *Candidatus Caldatribacterium californiense*. In FIG. 3, the amino acids shown in white on black are the amino acid residues identical to both amino acid sequences, the amino acids shown in black on a shaded grey background indicate positions where the amino acid residues in the sequences are similar, and "-" indicates a gap in a sequence.

<6> Expression and Purification of β-Xylosidase Enzyme Protein

Following sequence confirmation, the plasmid having the target gene was introduced into *E. coli* for protein expression using the heat shock method. The BL21 Star (DE3) strain provided in the Champion pET Directional TOPO Expression Kit (manufactured by Life Technologies Inc.) was used as the competent cell for the transformation. Expression of the target protein was induced by inoculating the *E. coli* having the target gene into an LB medium containing 100 mg/L of ampicillin, culturing to about $OD_{600}$=0.2 to 0.8, subsequently adding IPTG (isopropyl-β-D(-)-thiogalactopyranoside), and performing additional culturing for 5 to 20 hours. This operation yielded a weak expression of the enzyme protein encoded by the β-xylosidase candidate gene OJ1-273-1.

In order to improve the expression level of the enzyme protein, the β-xylosidase candidate gene OJ1-273-1 was incorporated into an expression vector pLEAD (manufactured by Nippon Gene Co., Ltd.) and transformed using the JM109 strain. The expression vector pLEAD has been shown to be effective for the expression of genes having a high GC content that are difficult to express using conventional *E. coli* expression vectors (Suzuki et al., J. Biochem., 1997, vol. 121, pp. 1031 to 1034; and Ishida and Oshima, J. Biochem., 2002, vol. 132., pp. 63 to 70). As a result, a strong expression of the enzyme protein encoded by the β-xylosidase candidate gene OJ1-273-1 was confirmed.

Specifically, using a pET101/D-TOPO vector having the β-xylosidase candidate gene OJ1-273-1 as a template, a forward primer including a nucleotide sequence represented by SEQ ID NO: 7 (5'-GTGATGTCGGTTCGGGTGAAGGAA-3': wherein three nucleotides (GTG) were added to the 5'-end of the nucleotide sequence represented by SEQ ID NO: 5, and the 5'-end was phosphorylated), and a reverse primer including a nucleotide sequence represented by SEQ ID NO: 8 (5'-TAGAGCTCTCATGCGGGCTCAACTTCAA-3': wherein a recognition sequence for the restriction enzyme SacI was added to the 5'-end of the nucleotide sequence represented by SEQ ID NO: 6, the SacI being a sequence used for vector insertion), a PCR product that had been amplified by KOD-Plus-Neo (manufactured by Toyobo Co., Ltd.) was inserted into a pLEADS vector, and transformed into an *E. coli* JM109 strain. Positive clones were selected by colony PCR and cultured in an LB liquid medium containing 50 mg/L of ampicillin at a temperature of 37° C. and 200 rpm for 17 to 20 hours, and then plasmids were prepared using a miniprep kit (Wizard plus SV Minipreps DNA Purification System, manufactured by Promega Corporation). Sequence confirmation of the prepared plasmids was performed using a 3730 DNA Analyzer sequencer manufactured by Life Technologies Corporation.

The transformed *E. coli* clone having the OJ1-273-1/pLEADS plasmid for which the sequence had been confirmed was inoculated into a Turbo Broth medium (manufactured by Athena Environmental Sciences, Inc.) containing 50 mg/L of ampicillin, and was cultured for about 20 hours to express the target protein. Following culturing, the *E. coli* was collected by centrifugation, and an amount of 50 mM Tris-HCl buffer (pH 8.0) equivalent to 1/10 of the volume of the culture liquid was added and suspended. Subsequently, a process consisting of 5 minutes disrupting and then 5 minutes of rest was repeated 7 or 8 times using an ultrasonic disrupter Astrason 3000 (manufactured by MISONIX Inc.), thus obtaining a crude extract of the gene recombinant *E. coli* containing the target protein. This gene recombinant *E. coli* crude extract was filtered through a filter (pore size φ=0.45 μm, manufactured by EMD Millipore Corporation), and the resulting filtrate was used as a gene recombinant *E. coli* homogeneous supernatant.

The gene recombinant *E. coli* homogeneous supernatant was loaded onto an ion exchange column HiTrap Q HP (manufactured by GE Healthcare, Inc.) equilibrated with a 50 mM Tris-HCl buffer (pH 8.0), and a medium-high pressure liquid chromatography system AKTA design (manufactured by GE Healthcare, Inc.) was used to fractionate proteins with a concentration gradient of 0 to 50% in a 50 mM Tris-HCl buffer (pH 8.0) containing 1 M of NaCl. The fractions exhibiting β-xylosidase activity were pooled, and a centrifugal ultrafiltration membrane VIVASPIN 20 (manufactured by Sartorius stedim Biotech SA) was used to exchange the buffer to a 50 mM Tris-HCl buffer (pH 8.0) containing 750 mM of ammonium sulfate. The fractions with β-xylosidase activity following the buffer exchange were loaded onto a hydrophobic interaction separation column HiTrap Phenyl HP (manufactured by GE Healthcare, Inc.) equilibrated with the same buffer solution, and the proteins were fractionated with a concentration gradient of 0 to 100% in a 50 mM Tris-HCl buffer (pH 8.0). The fractions exhibiting β-xylosidase activity were pooled and then concentrated by using the VIVASPIN 20 until the liquid volume reached about 8 mL. The concentrated sample was loaded onto a gel filtration column Hiload 26/60 superdex 200 pg (manufactured by GE Healthcare, Inc.) equilibrated with a 50 mM Tris-HCl buffer (pH 8.0) containing 150 mM of NaCl, and was fractionated by passing a volume of the same buffer equivalent to 1 to 1.5 times the column volume through the column at a flow rate of 2 to 3 mL/min. The fractions exhibiting β-xylosidase activity were pooled, a buffer exchange to a 1 mM phosphate buffer (pH 6.8) and subsequent concentration were performed using the VIVASPIN 20, the concentrated sample was loaded onto a hydroxyapatite column CHT 5-1 (manufactured by Bio-Rad Laboratories, Inc.) equilibrated with the same buffer, and the proteins were fractionated with a concentration gradient of 0 to 100% in a 400 mM phosphate buffer (pH 6.8). The fractions exhibiting β-xylosidase activity were once again pooled, and a buffer exchange to a 50 mM Tris-HCl buffer (pH 8.0) and subsequent concentration were performed, yielding a purified enzyme with a final concentration of about 1 mg/mL.

The gene recombinant *E. coli* homogenous supernatant and the purified enzyme (purified β-xylosidase enzyme protein) were checked by SDS-PAGE (SDS-polyacrylamide gel electrophoresis) analysis. The SDS-PAGE of the gene recombinant *E. coli* homogenous supernatant and the purified enzyme was performed using a Mini-PROTEAN TGX Stain-Free gel (manufactured by Bio-Rad Laboratories, Inc.). The supernatant and the purified enzyme were each mixed with Tris-SDS βME treatment solution (manufactured by Cosmo Bio Co. Ltd.) at 1:1, and following treatment of the thus obtained electrophoresis samples at 100° C. for 10 minutes, 10 μL of the gene recombinant *E. coli* homogenous supernatant and 2 μg of the purified enzyme respectively were subjected to electrophoresis. Following completion of the electrophoresis, the protein bands were visualized and detected by CBB staining.

FIG. 4 shows the SDS-PAGE analysis results of the gene recombinant *E. coli* homogenous supernatant prepared from the transformed *E. coli* into which the OJ1M-273-1 gene had been introduced, and the purified enzyme produced from the gene recombinant *E. coli* homogenous supernatant. The figure shows an electrophoretic pattern in which lane 1 represents a protein mass marker, lane 2 represents the gene recombinant *E. coli* homogenous supernatant, and lane 3 represents the purified enzyme. The results revealed a strong band in the gene recombinant *E. coli* homogenous supernatant (lane 2) near the molecular weight of 78.9 kDa expected from the amino acid sequence (SEQ ID NO: 2), and a single band corresponding with this band (indicated by an arrow in the figure) was observed in the purified enzyme (lane 3).

<7> Measurement of β-Xylosidase Activity Against PNPX Substrate (PNPX Hydrolysis Activity)

PNPX was used as the substrate for measuring the β-xylosidase activity. A solution prepared by dissolving PNPX (manufactured by Sigma-Aldrich Co. LLC.) in water to obtain a prescribed final concentration was used as the substrate solution. The PNPX substrate solutions used in the experiments described below all used aqueous solutions of PNPX prepared by the above method. In the measurements, a solution prepared by diluting the purified enzyme obtained in section <6> above with a 0.05 M Tris-HCl buffer (pH 8.0) to obtain a concentration of 0.1 to 0.01 mg/mL was used.

The reaction solution was composed of 6 µL of the diluted purified enzyme, 294 µL of purified water, 150 µL of a 200 mM acetate buffer (pH 5), and 150 µL of a 20 mM PNPX aqueous solution.

The reaction was performed at 60° C. to 115° C. for 10 minutes using a ReactiTherm (manufactured by Thermo Fisher Scientific Inc.). A glass vial with a volume of 1.5 mL was used as the reaction vessel, and the inside of the vial was pre-coated with a 1.5% by mass aqueous solution of BSA in order to suppress enzyme protein adsorption. In all measurements, a mixed solution prepared by replacing the gene recombinant *E. coli* homogenous supernatant or the purified enzyme with a 50 mM Tris-HCl buffer (pH 8.0) and then reacting the solution under the same conditions was used as a control. Further, the mixed solution containing the enzyme (the gene recombinant *E. coli* homogenous supernatant or the purified enzyme), the purified water and the buffer was held at the reaction temperature for five minutes (pre-incubation), the substrate solution was then added, and the reaction was performed. In each case, following completion of the 10-minute reaction, the reaction was halted by adding a 0.2 M Na$_2$CO$_3$ solution to the reaction solution in a volume equal to that of the mixed solution, and the resulting mixture was then centrifuged for 5 minutes to obtain a supernatant. The amount of p-nitrophenol in the supernatant was determined by measuring the absorbance at 420 nm using a spectrophotometer, calculating the amount of p-nitrophenol in the supernatant using a calibration curve prepared with p-nitrophenol, and then determining the amount of p-nitrophenol produced by the enzymatic hydrolysis on the basis of the difference from the control. The enzymatic activity for producing 1 µmol of p-nitrophenol per minute was defined as 1 U, and the value obtained by dividing this activity by the amount of protein was defined as the specific activity (U/mg). Each measurement was performed for three independent experiments, and a mean value and a standard error were determined.

As a result, β-xylosidase activity (PNPX hydrolysis activity) was confirmed both in the case when the gene recombinant *E. coli* homogenous supernatant was used and the case when the purified enzyme was used.

<8> Substrate Specificity of OJ1M-273-1

The hydrolysis activity of the enzyme protein (OJ1M-273-1) encoded by the OJ1M-273-1 gene against various cellulose substrates and hemicellulose substrates was investigated. For the substrates, CMC (manufactured by Sigma-Aldrich Co. LLC.), xylan (derived from beech wood, manufactured by Sigma-Aldrich Co. LLC.), arabinan (derived from sugar beet, manufactured by Sigma-Aldrich Co. LLC.), arabinogalactan (derived from larch wood, manufactured by Sigma-Aldrich Co. LLC.), PNPX (manufactured by Sigma-Aldrich Co. LLC.), PNPG (manufactured by Sigma-Aldrich Co. LLC.), PNPAF (manufactured by Sigma-Aldrich Co. LLC.), PNPAP (manufactured by Sigma-Aldrich Co. LLC.), PNPGA (manufactured by Sigma-Aldrich Co. LLC.), PNPFP (manufactured by Sigma-Aldrich Co. LLC.), PNPRP (manufactured by Sigma-Aldrich Co. LLC.), PNPMP (manufactured by Sigma-Aldrich Co. LLC.), PNPadX (manufactured by Sigma-Aldrich Co. LLC.) and PNPbdFP (manufactured by Sigma-Aldrich Co. LLC.) were used.

Specifically, in the case of the substrates other than CMC, xylan, arabinan and arabinogalactan, with the exceptions of using the purified enzyme diluted to 0.02 mg/mL and a 20 mM aqueous solution of each substrate, and performing the reactions at 105° C., the same method as that described above in section <7> was used to determine the amount of p-nitrophenol produced by the enzymatic hydrolysis, and then calculate the specific activity (U/mg).

When CMC, xylan, arabinan or arabinogalactan was used as the substrate, with the exceptions of using the purified enzyme diluted to 0.02 mg/mL and a 1% by mass aqueous solution of each substrate, and performing the reaction at 105° C., reaction was first performed in the same manner as that described above in section <7>, and following completion of the reaction, 3,5-dinitrosalicylic acid reagent (DNS solution) was added to the reaction solution in a volume equal to that of the reaction solution, and the resulting mixture was heated at 100° C. for 5 minutes, cooled on ice for 5 minutes, and then centrifuged at 17,500 g for 5 minutes at room temperature to obtain a supernatant. The amount of reducing sugars within the supernatant was determined by measuring the absorbance at 540 nm using a spectrophotometer, calculating the amount of reducing sugars using a calibration curve prepared with glucose (specifically, a calibration curve prepared with xylose in the case where xylan was used as the substrate, or a calibration curve prepared with arabinose in the case where arabinan or arabinogalactan was used as the substrate), and then calculating the amount of reducing sugars produced by the enzymatic hydrolysis based on the difference from the control. The enzymatic activity for producing 1 µmol of reducing sugars per minute was defined as 1 U, and the value obtained by dividing this activity by the amount of protein was defined as the specific activity (U/mg).

Figure 5:
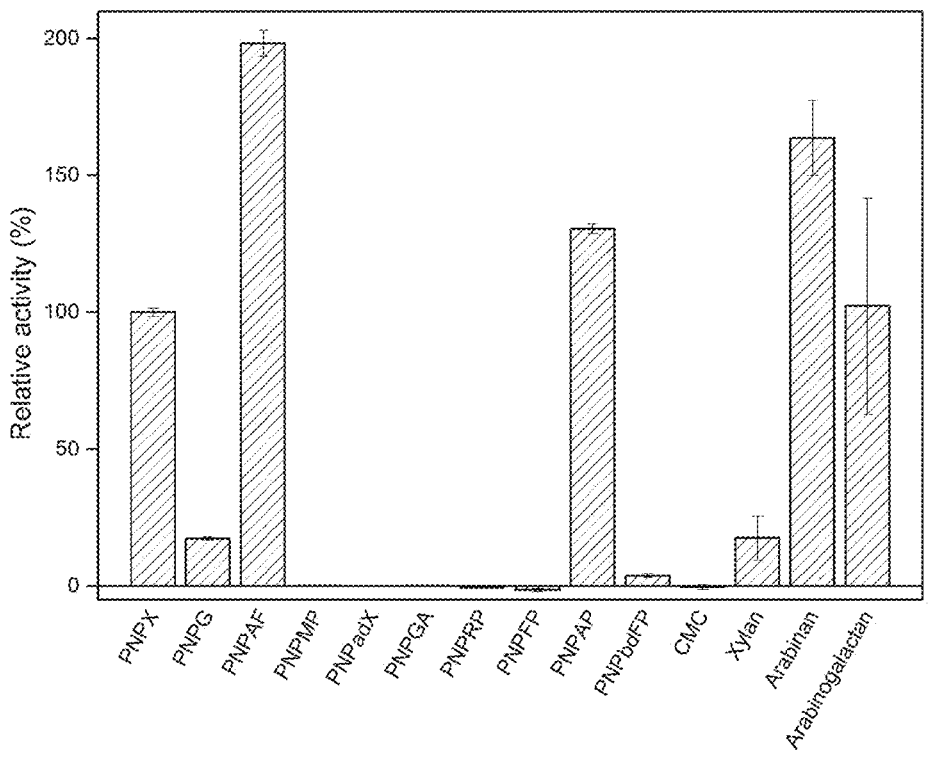
FIG. 5 is a diagram showing the results of measuring the hydrolysis activity against various substrates (namely, the relative activity when the hydrolysis activity against PNPX is deemed to be 100%) of the OJ1M-273-1 protein expressed in *E. coli* in Example 1.

The measurement results are shown in FIG. 5. The enzymatic activity values are each shown as a relative activity (%) with the hydrolysis activity against PNPX deemed to be 100%. The results revealed that OJ1M-273-1 exhibited a high level of hydrolysis activity against PNPX, PNPAF, PNPAP, arabinan and arabinogalactan, exhibited weak hydrolysis activity against PNPG and xylan, and exhibited almost no hydrolysis activity against the remaining substrates.

<9> Kinetics of OJ1M-273-1 β-Xylosidase

The maximum initial rate (Vmax) of hydrolysis, the Michaelis constant (Km) and the catalytic efficiency (Kcat/Km) were investigated for PNP substrate hydrolysis by OJ1M-273-1. With the exceptions of using PNPX aqueous solutions having concentrations of 0.2 mM, 0.5 mM, 1 mM, 3 mM, 5 mM, 10 mM and 20 mM, using PNPAF aqueous solutions and PNPAP aqueous solutions each having concentrations of 1 mM, 3 mM, 5 mM, 10 mM, 20 mM, 30 mM, 40 mM, 50 mM and 60 mM, using an enzyme that had been diluted to 0.01 mg/mL, and performing the reactions at 105° C., the kinetics measurements were performed in the same manner as that described above in section <7>, and the PNP substrate hydrolysis activity (U/mg) was calculated in each case. The maximum initial rate (Vmax) and the Michaelis constant (Km) were determined by fitting to the Michaelis-Menten model using the data analysis software Origin (manufactured by LightStone Corporation), and the resulting numerical values were used to calculate the catalytic efficiency (Kcat/Km).

The results are shown in Table 2. The maximum initial rate was greatest when the substrate was PNPAF, but the catalytic efficiency was greatest when the substrate was PNPX. This indicates that PNPX is the most appropriate substrate for OJ1M-273-1.

|       | Vmax (U/mg) | Km (mM) | Kcat/Km (mM$^{-1}$sec$^{-1}$) |
|-------|-------------|---------|-------------------------------|
| PNPX  | 86.0        | 0.44    | 259.8                         |
| PNPAF | 914.5       | 13.7    | 87.7                          |
| PNPAP | 838.5       | 20.6    | 53.6                          |

<10> pH and Temperature Dependencies of β-Xylosidase Activity Against PNPX Substrate The temperature dependency and the pH dependency of the PNPX hydrolysis activity of the enzyme protein (OJ1M-273-1) encoded by the OJ1M-273-1 gene were investigated. In the measurements, a purified enzyme solution prepared by diluting the purified enzyme obtained in section <6> above to obtain a concentration of 0.1 mg/mL was used.

Measurement of the temperature dependency of the PNPX hydrolysis activity of the purified OJ1M-273-1 was conducted in the same manner as that described above in section <7>, with the exception of performing measurements at reaction temperatures of 60, 70, 80, 90, 95, 100, 105, 110, and 115° C., and for each temperature, the amount of p-nitrophenol produced by the enzymatic hydrolysis was determined and the PNPX hydrolysis activity (U/mg) was calculated.

Figure 6:
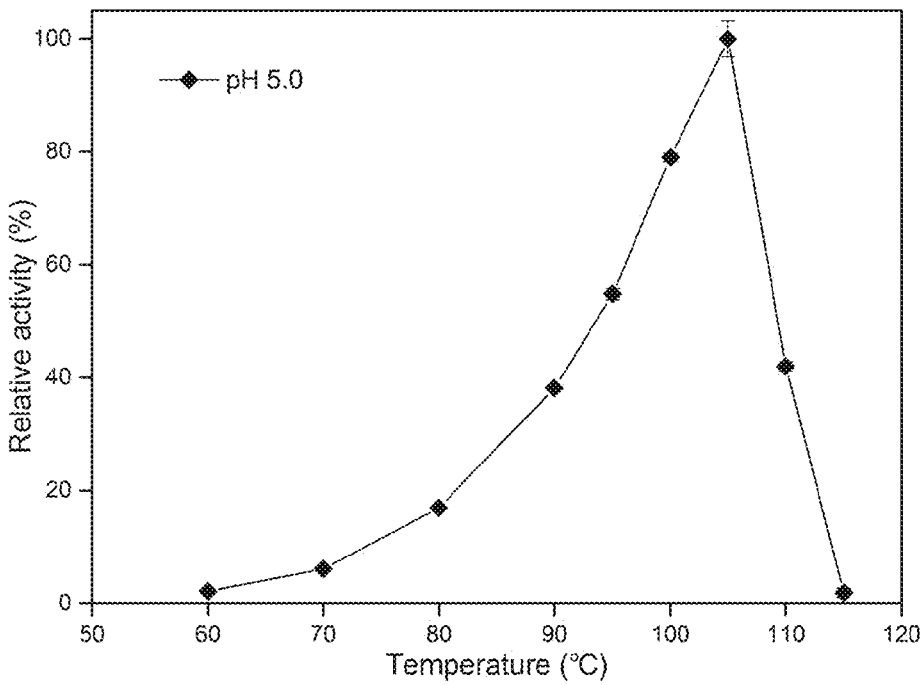
FIG. 6 is a diagram showing the results of measuring the PNPX hydrolysis activity (pH 5.0) at various temperatures (namely, the relative activity when the hydrolysis activity at 105° C. is deemed to be 100%) of the OJ1M-273-1 protein expressed in *E. coli* in Example 1.

The results are shown in FIG. 6. The enzymatic activity values are shown as relative activity values (%), with the highest hydrolysis activity at 105° C. deemed to be 100%. OJ1M-273-1 exhibited PNPX hydrolysis activity within a temperature range from 60 to 110° C. (FIG. 6). In the temperature range from 60 to 105° C., the PNPX hydrolysis activity increased as the enzymatic reaction temperature was increased, and the optimum temperature ($T_{opt}$) showing the highest activity was 105° C. When the enzymatic reaction temperature was increased beyond 105° C., the PNPX hydrolysis activity decreased rapidly.

Measurement of the pH dependency of the PNPX hydrolysis activity of the purified OJ1M-273-1 was conducted in the same manner as that described above in section <7>, with the exceptions of using a mixed solution containing a purified enzyme solution diluted to 0.1 mg/mL and 150 μL of McIlvaine's buffer (pH 3 to 8) and performing the reaction at 105° C., and for each of the pH values, the amount of p-nitrophenol produced by the enzymatic hydrolysis was determined and the PNPX hydrolysis activity (U/mg) was calculated.

Figure 7:
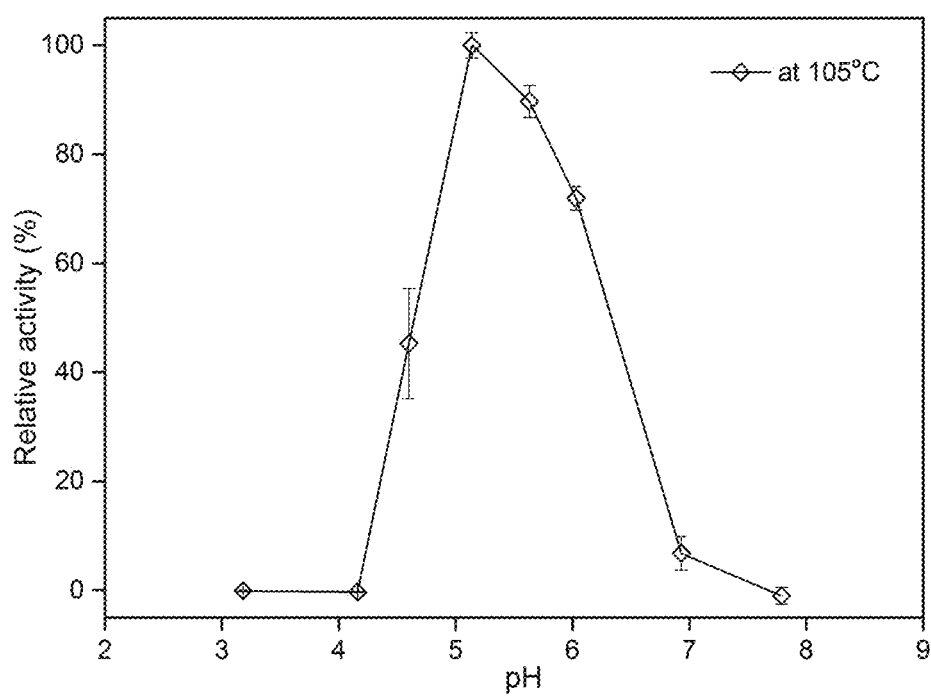
FIG. 7 is a diagram showing the results of measuring the PNPX hydrolysis activity (105° C.) at various pH values (namely, the relative activity when the hydrolysis activity at pH 5.0 is deemed to be 100%) of the OJ1M-273-1 protein expressed in *E. coli* in Example 1.

The results are shown in FIG. 7. The enzymatic activity values are shown as relative activity values (%), with the highest hydrolysis activity at pH 5.0 deemed to be 100%. For the pH values, the actual measurement value obtained for the mixed solution containing the substrate, the buffer and the enzyme was plotted. OJ1M-273-1 exhibited PNPX hydrolysis activity within a pH range from pH 4.5 to 7. The optimum pH value was 5.14 (actual measurement value for the mixed solution containing the substrate, the buffer and the enzyme).

<11> Thermal Stability Measurement of β-Xylosidase

The thermal stability of the PNPX hydrolysis activity of OJ1M-273-1 was investigated. Measurements were performed using a purified enzyme solution prepared by diluting the purified enzyme obtained in section <6> above to obtain a concentration of 0.1 mg/mL Specifically, a mixed solution containing 6 μL of the purified enzyme solution (0.1 mg/mL), 294 μL of purified water and 150 μL of a 200 mM acetate buffer (pH 5.0) was held at a temperature of 85° C., 90° C., 95° C., 100° C. or 105° C. for a period of 0, 30, 60, 120 or 240 minutes (pre-incubation), and the PNPX hydrolysis activity was then measured at 95° C. in the same manner as that described above in section <7>, the amount of p-nitrophenol produced by the enzymatic hydrolysis was determined, and the relative activity (U/mg) was calculated.

Figure 8:
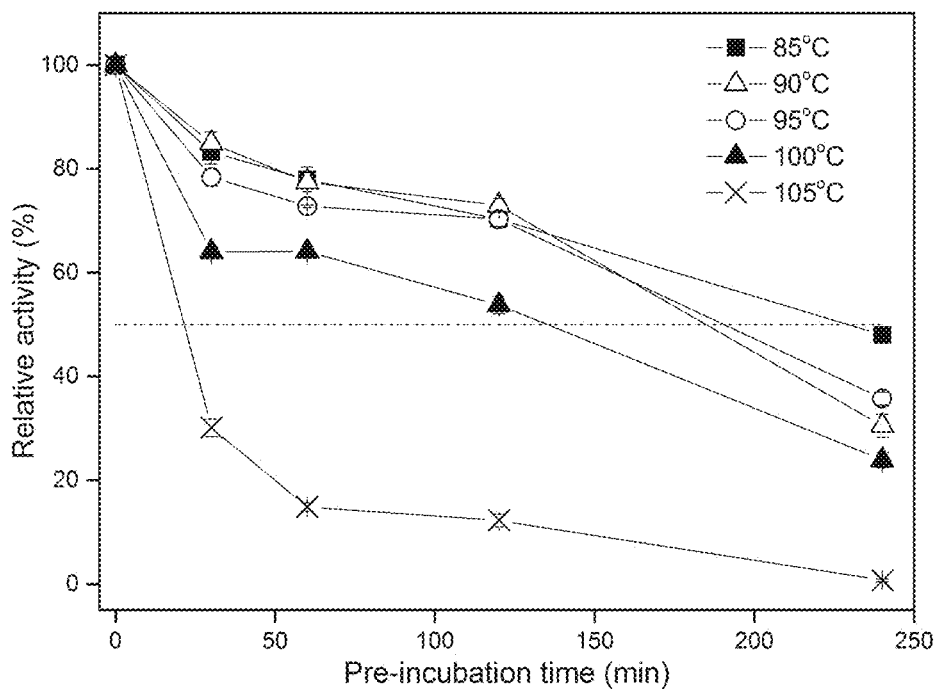
FIG. 8 is a diagram showing the results of measuring the thermal stability (at pH 5.0) of the PNPX hydrolysis activity (namely, the relative value when the hydrolysis activity of an untreated sample (holding time: 0 minutes) is deemed to be 100%) of the OJ1M-273-1 protein expressed in *E. coli* in Example 1.

The measurement results are shown in FIG. 8. The enzymatic activity is shown as a relative activity value (%), with the activity for an untreated sample (holding time: 0 minutes) deemed to be 100%. The holding time necessary for the enzymatic activity to decrease to 50% of that of the untreated sample was deemed the half life $T_{half}$. The $T_{half}$ value for OJ1M-273-1 was about 240 minutes when the holding temperature was 85° C., about 180 minutes when the holding temperature was 90° C. or 95° C., and about 130 minutes when the holding temperature was 100° C. On the other hand, when the holding temperature was set to 105° C., the PNPX hydrolysis activity decreased rapidly, and fell to about 30% after 30 minutes.

[Sequence Listings]

The invention claimed is:

1. A thermostable β-xylosidase comprising a polypeptide consisting of the amino acid sequence of SEQ ID NO:1 or 2 and at least one moiety selected from the group consisting of a Fibronectin type III domain, a linker region, a signal peptide, a tag and cellulose binding module.

2. A glycoside hydrolase mixture, comprising the thermostable β-xylosidase according to claim 1 and at least one other glycoside hydrolase.

3. A method for producing a lignocellulose degradation product, the method comprising generating the lignocellulose degradation product by bringing a material containing lignocellulose into contact with the thermostable β-xylosidase according to claim 1.

4. A method for producing a lignocellulose degradation product, the method comprising generating the lignocellulose degradation product by bringing a material containing lignocellulose into contact with the glycoside hydrolase mixture according to claim 2.

* * * * *

SEQUENCE LISTING

```
<160> NUMBER OF SEQ ID NOS: 9

<210> SEQ ID NO 1
<211> LENGTH: 725
<212> TYPE: PRT
<213> ORGANISM: Unknown
<220> FEATURE:
<223> OTHER INFORMATION: Open reading frame OJ1M-273
<220> FEATURE:
<221> NAME/KEY: UNSURE
<222> LOCATION: (300)..(318)
<223> OTHER INFORMATION: Xaa stands for unspecified amino acid.
```

<400> SEQUENCE: 1

```
Met Ser Val Arg Val Lys Glu Leu Leu Ala Lys Met Thr Leu Glu Glu
1               5                   10                  15

Lys Val Ala Gln Leu Gly Ser Ile Ser Val His Arg Leu Met Thr Asp
            20                  25                  30

Gly Lys Phe Asp Ile Ala Lys Ala Arg Glu Leu Leu Lys His Gly Ile
        35                  40                  45

Gly Gln Ile Thr Arg Val Ala Gly Gly Ser Asn Leu Pro Pro Lys Glu
    50                  55                  60

Ala Ala Gln Leu Ala Asn Glu Ile Gln Arg Phe Leu Ile Glu Glu Thr
65                  70                  75                  80

Arg Leu Gly Ile Pro Ala Ile Val His Glu Glu Cys Leu Ser Gly Leu
                85                  90                  95

Met Ala Arg Gly Ser Thr Thr Phe Pro Gln Ala Ile Asn Leu Ala Ser
            100                 105                 110

Thr Phe Asp Pro Asp Leu Val Arg Glu Met Thr Thr Val Ile Arg Lys
        115                 120                 125

Glu Met Arg Ala Val Gly Ala His Gln Gly Leu Ser Pro Val Leu Asp
    130                 135                 140

Val Leu Arg Asp Pro Arg Trp Gly Arg Thr Glu Glu Thr Phe Gly Glu
145                 150                 155                 160

Asp Pro Tyr Leu Ile Ala Cys Met Ala Val Ala Tyr Ile Ser Gly Leu
                165                 170                 175

Gln Gly Glu Asp Leu Arg Gln Gly Val Ile Ala Thr Ala Lys His Phe
            180                 185                 190

Ser Gly His Gly Trp Pro Glu Gly Gly Arg Asn Cys Ala Pro Leu His
        195                 200                 205

Val Gly Pro Arg Glu Phe Arg Glu Val Leu Ser Phe Pro Phe Glu Ala
    210                 215                 220

Ala Val Arg Val Ala Arg Val Gln Ser Val Met Asn Ala Tyr His Asp
225                 230                 235                 240

Ile Asp Gly Ile Pro Cys Ala Ala Ser Arg Glu Leu Leu Thr Asp Leu
                245                 250                 255

Leu Arg Gly Glu Trp Gly Phe Asp Gly Ile Val Val Ser Asp Tyr Ala
            260                 265                 270

Ala Val His Met Leu Phe Asn Val His Arg Val Ala Val Asp Glu Lys
        275                 280                 285

Asp Ala Ala Cys Gln Ala Leu Tyr Ala Gly Ile Xaa Xaa Xaa Xaa Xaa
    290                 295                 300

Xaa Xaa Xaa Xaa Xaa Xaa Xaa Xaa Xaa Xaa Xaa Xaa Xaa Xaa Leu Phe
305                 310                 315                 320

Asp Asn Pro Pro Phe Val Asp Pro Glu Ala Ala Pro Ser Val Phe Asp
                325                 330                 335

Ala Pro Glu His Arg Gln Leu Ala Arg Leu Leu Ala Gln Lys Ser Ile
            340                 345                 350

Val Leu Leu Lys Asn Asp Gly Asn Leu Leu Pro Leu Arg Lys Asp Leu
        355                 360                 365

Ser Ser Ile Ala Val Ile Gly Pro Asn Ala Asp Asp Pro Arg Asn Met
    370                 375                 380

Leu Gly Asp Tyr Ala Tyr Val Ala His Leu Asp Leu Lys Glu Thr Pro
385                 390                 395                 400

Val Pro Ile Val Thr Val Leu Glu Gly Ile Lys Ala Lys Val Ser Pro
```

```
            405                 410                 415
Ala Thr Lys Val Leu Tyr Ala Lys Gly Cys Glu Val Leu Asp Gly Thr
            420                 425                 430

Thr Glu Gly Ile Ala Glu Ala Val Glu Val Ala Lys Gln Ala Glu Val
        435                 440                 445

Val Val Leu Val Val Gly Asp Arg Ser Gly Leu Phe Gly Lys Gly Thr
    450                 455                 460

Val Gly Glu Gly Cys Asp Arg Val Asp Leu Arg Leu Pro Gly His Gln
465                 470                 475                 480

Glu Glu Leu Val Lys Ala Val Val Glu Thr Gly Lys Pro Val Val Leu
                485                 490                 495

Val Leu Ile Asn Gly Arg Pro Val Thr Leu Gly Glu Leu Val Asp Lys
            500                 505                 510

Ile Pro Ala Ile Val Glu Ala Trp Phe Pro Gly Glu Gly Gly Asn
        515                 520                 525

Ala Val Ala Asp Val Leu Phe Gly Asp Val Asn Pro Gly Gly Lys Leu
    530                 535                 540

Pro Ile Thr Phe Pro Lys Val Val Gly Gln Val Pro Leu His Tyr Ser
545                 550                 555                 560

Arg Ala Pro Leu Ser His Arg Asp Tyr Val Glu Met Lys Asn Val Pro
                565                 570                 575

Gln Phe Pro Phe Gly His Gly Leu Ser Tyr Thr Lys Phe Glu Tyr Ser
            580                 585                 590

Asp Leu Thr Ile Ala Pro Glu Lys Ile Ser Pro Ala Gly Thr Val Ser
        595                 600                 605

Ile Ser Val Thr Val Lys Asn Val Gly Asp Arg Gly Asp Glu Val
    610                 615                 620

Val Gln Leu Tyr Val Arg Asp Val Ala Ser Arg Val Arg Pro Val
625                 630                 635                 640

Lys Glu Leu Lys Gly Phe Lys Arg Val Thr Leu Lys Pro Gly Glu Ala
                645                 650                 655

Lys Arg Val Thr Phe His Leu Ser Ala Asp Gln Leu Ala Phe Tyr Asp
            660                 665                 670

Arg Ala Met Arg Phe Val Val Glu Pro Gly Thr Ile Glu Val Met Val
        675                 680                 685

Gly Ser Ser Glu Asp Ile Arg Leu Thr Gly Lys Phe Glu Ile Val
    690                 695                 700

Gly Asp Val Arg Glu Val Pro Gly Glu Arg Val Met Phe Thr Arg Val
705                 710                 715                 720

Glu Val Glu Pro Ala
            725

<210> SEQ ID NO 2
<211> LENGTH: 748
<212> TYPE: PRT
<213> ORGANISM: Unknown
<220> FEATURE:
<223> OTHER INFORMATION: Amino acid sequence of OJ1M-273-1

<400> SEQUENCE: 2

Met Ser Val Arg Val Lys Glu Leu Leu Ala Lys Met Thr Leu Glu Glu
1               5                   10                  15

Lys Val Ala Gln Leu Gly Ser Ile Ser Val His Arg Leu Met Thr Asp
            20                  25                  30

Gly Lys Phe Asp Ile Ala Lys Ala Arg Glu Leu Leu Lys His Gly Ile
```

```
            35                  40                  45
Gly Gln Ile Thr Arg Val Ala Gly Gly Ser Asp Leu Pro Pro Lys Glu
 50                  55                  60

Ala Ala Gln Leu Ala Asn Glu Ile Gln Arg Phe Leu Ile Glu Glu Thr
 65                  70                  75                  80

Arg Leu Gly Ile Pro Ala Ile Val His Glu Cys Leu Ser Gly Leu
                 85                  90                  95

Met Ala Arg Gly Ser Thr Thr Phe Pro Gln Ala Ile Asn Leu Ala Ser
                100                 105                 110

Thr Phe Asp Pro Asp Leu Val Arg Glu Met Thr Thr Val Ile Arg Lys
                115                 120                 125

Glu Met Arg Ala Val Gly Ala His Gln Gly Leu Ser Pro Val Leu Asp
                130                 135                 140

Val Leu Arg Asp Pro Arg Trp Gly Arg Thr Glu Thr Phe Gly Glu
145                 150                 155                 160

Asp Pro Tyr Leu Ile Ala Cys Met Ala Val Ala Tyr Ile Ser Gly Leu
                165                 170                 175

Gln Gly Glu Asp Leu Arg Gln Gly Val Ile Ala Thr Ala Lys His Phe
                180                 185                 190

Ser Gly His Gly Trp Pro Glu Gly Gly Arg Asn Cys Ala Pro Leu His
                195                 200                 205

Val Gly Pro Arg Glu Phe Arg Glu Val Leu Ser Phe Pro Phe Glu Ala
                210                 215                 220

Ala Val Arg Val Ala Arg Val Gln Ser Val Met Asn Ala Tyr His Asp
225                 230                 235                 240

Ile Asp Gly Ile Pro Cys Ala Ala Ser Arg Glu Leu Leu Thr Asp Leu
                245                 250                 255

Leu Arg Gly Glu Trp Gly Phe Asp Gly Ile Val Val Ser Asp Tyr Ala
                260                 265                 270

Ala Val His Met Leu Phe Asn Val His Arg Val Ala Val Asp Glu Lys
                275                 280                 285

Asp Ala Ala Cys Gln Ala Leu Tyr Ala Gly Ile Asp Ile Glu Leu Pro
                290                 295                 300

Asp Leu Asn Cys Tyr Ala Lys Leu Ile Asp Ala Val Arg Glu Gly Leu
305                 310                 315                 320

Ile Ser Glu Ala Ile Val Asp Glu Ala Val Arg Arg Val Leu Thr Val
                325                 330                 335

Lys Glu Arg Leu Gly Leu Phe Asp Asn Pro Pro Phe Val Asp Pro Glu
                340                 345                 350

Ala Ala Pro Ser Val Phe Asp Ala Pro Glu His Arg Gln Leu Ala Arg
                355                 360                 365

Leu Leu Ala Gln Lys Ser Ile Val Leu Leu Lys Asn Asp Gly Asn Leu
                370                 375                 380

Leu Pro Leu Arg Lys Asp Leu Ser Gly Ile Ala Val Ile Gly Pro Asn
385                 390                 395                 400

Ala Asp Asp Pro Arg Asn Met Leu Gly Asp Tyr Ala Tyr Val Ala His
                405                 410                 415

Leu Asp Leu Lys Glu Thr Pro Val Pro Ile Val Thr Val Leu Glu Gly
                420                 425                 430

Ile Lys Ala Lys Val Ser Pro Ala Thr Lys Val Leu Tyr Ala Lys Gly
                435                 440                 445

Cys Glu Val Leu Asp Gly Thr Thr Glu Gly Ile Ala Glu Ala Val Glu
450                 455                 460
```

Val Ala Lys Gln Ala Glu Val Val Leu Val Val Gly Asp Arg Ser
465                 470                 475                 480

Gly Leu Phe Gly Lys Gly Thr Val Gly Glu Gly Cys Asp Arg Val Asp
                485                 490                 495

Leu Arg Leu Pro Gly His Gln Glu Glu Leu Val Lys Ala Val Val Glu
            500                 505                 510

Thr Gly Lys Pro Val Val Leu Val Leu Ile Asn Gly Arg Pro Val Thr
        515                 520                 525

Leu Gly Glu Leu Val Asp Lys Ile Pro Ala Ile Val Glu Ala Trp Phe
    530                 535                 540

Pro Gly Glu Glu Gly Gly Asn Ala Val Ala Asp Val Leu Phe Gly Asp
545                 550                 555                 560

Val Asn Pro Gly Gly Lys Leu Pro Ile Thr Phe Pro Lys Val Val Gly
                565                 570                 575

Gln Val Pro Leu His Tyr Ser Arg Ala Pro Leu Ser His Arg Asp Tyr
            580                 585                 590

Val Glu Met Lys Asn Val Pro Gln Phe Pro Phe Gly His Gly Leu Ser
        595                 600                 605

Tyr Thr Lys Phe Glu Tyr Ser Asp Leu Thr Ile Ala Pro Glu Lys Ile
    610                 615                 620

Ser Pro Ala Gly Thr Val Ser Ile Ser Val Thr Val Lys Asn Val Gly
625                 630                 635                 640

Asp Arg Glu Gly Asp Glu Val Val Gln Leu Tyr Val Arg Asp Val Val
                645                 650                 655

Ala Ser Arg Val Arg Pro Val Lys Glu Leu Lys Gly Phe Lys Arg Val
            660                 665                 670

Thr Leu Lys Pro Gly Glu Ala Lys Arg Val Thr Phe His Leu Ser Ala
        675                 680                 685

Asp Gln Leu Ala Phe Tyr Asp Arg Ala Met Arg Phe Val Val Glu Pro
    690                 695                 700

Gly Thr Ile Glu Val Met Val Gly Ser Ser Ser Glu Asp Ile Arg Leu
705                 710                 715                 720

Thr Gly Lys Phe Glu Ile Val Gly Asp Val Arg Glu Val Pro Gly Glu
                725                 730                 735

Arg Val Met Phe Thr Gln Val Glu Val Glu Pro Ala
            740                 745

<210> SEQ ID NO 3
<211> LENGTH: 2178
<212> TYPE: DNA
<213> ORGANISM: Unknown
<220> FEATURE:
<223> OTHER INFORMATION: Open reading frame OJ1M-273
<220> FEATURE:
<221> NAME/KEY: misc_feature
<222> LOCATION: (900)..(954)
<223> OTHER INFORMATION: n stands for unspecified nucleic acid.

<400> SEQUENCE: 3
atgtcggttc gggtgaagga acttttggcg aagatgaccc ttgaggagaa agttgcccaa     60
cttggttcaa tttctgtcca caggctcatg accgacggca aatttgacat tgcaaaggct    120
cgtgagttgc tcaagcatgg catcggtcaa atcacccgcg tcgctggcgg cagcaattta    180
ccgccaaagg aagcagcaca actcgccaac gaaattcagc gcttcctcat tgaagagacg    240
aggttgggaa ttcccgctat cgtgcacgaa gaatgcctca gcggattgat ggcgcgaggg    300

```
tcaacgactt tccccaagc catcaacttg gcaagcactt ttgaccccga tttggttcgg        360
gagatgacaa cggtaattcg caaggaaatg cgcgccgtcg gagcgcatca aggtttgtcg        420
cctgtcttgg atgtccttcg cgacccgcga tggggacgga cggaagaaac tttcggcgaa        480
gacccatact tgattgcctg catggcggtc gcttacatct ctggcttgca aggcgaagat        540
ttgaggcagg gcgtcattgc taccgcaaag cacttttcag gtcacggttg gcctgaaggc        600
ggtcgtaact gtgccccact tcatgtcggt ccgagagagt tcagggaagt cctctcattc        660 cccttttgaag cggcagttag ggtggcaaga gttcagtcgg tcatgaacgc ttaccatgac        720
attgatggca tccctgcgc tgcttcccgc gagttgttga ctgaccttct gcgaggcgaa        780
tggggatttg acggcatcgt cgtttcagat tacgccgccg tccacatgct tttcaatgtc        840 cacaggttg cagttgacga aaagatgca gcctgccaag cccttatgc aggcattgan        900 nnnnnnnnnn nnnnnnnnnn nnnnnnnnnn nnnnnnnnnn nnnnnnnnnn nnnnttgttt        960
gacaatccgc cgttcgttga ccccgaagca gcaccttccg ttttgacgc ccctgaacac       1020 cgccaactcg ctcggttgct cgctcaaaag tcaattgtgt tgctcaaaaa cgatggtaac       1080
ttgcttccgc tacgaaaaga tttgtcaagc atcgccgtca tcggtccaaa cgccgacgac       1140
ccacgaaaca tgctcggcga ttacgcttat gtggctcact tggacttgaa ggaaacgcct       1200
gtgccaattg tgactgtcct tgaaggcatc aaggcgaaag tttcgcccgc cacgaaagtc       1260
ctctacgcca aggttgcga agttctggac gggcaacgg aaggaatcgc cgaagcggtt        1320
gaagtcgcaa acaagcgga agtcgtcgtc ttggtcgtcg gtgaccgctc aggcttgttc       1380
ggcaaaggga cggtcggcga aggttgcgat agggttgact tgaggcttcc cggtcaccaa       1440
gaggaacttg tcaaggctgt ggttgaaact ggcaagcccg tcgtcttggt tctcatcaac       1500
ggtcgccccg ttacgcttgg agaactcgtt gacaaaattc cggcaatagt tgaggcttgg       1560
tttccgggtg aggaaggtgg caatgctgtc gctgatgttt tgtttggcga tgtcaaccca       1620
ggcggcaaac tccccatcac cttcccgaaa gtcgtcggtc aagtcccgct gcactatagc       1680
cgagcaccgc tttcgcaccg cgattatgtg gagatgaaaa atgtcccgca attcccattc       1740
gggcacgggg tcagttacac gaagtttgaa tacagcgact tgacaattgc ccctgagaaa       1800
atttcacccg caggcacagt ctccatctcc gtgacggtca aaaatgtcgg cgaccgagaa       1860
ggtgacgagg ttgtccagtt gtatgtccgc gatgtcgtcg caagccgcgt ccgacccgtc       1920
aaggaactca aggtttcaa gcgagtgacg ctgaagccag gtgaggctaa acgggtgact       1980
ttccacctgt ccgctgacca gttggctttt tacgaccgag cgatgaggtt cgtggttgag       2040
ccaggaacaa ttgaggtcat ggtcggaagt tcgtctgagg acattaggct caccggcaaa       2100
tttgaaattg tcggcgatgt cagggaagtt ccaggtgaaa gggtcatgtt cactcgggtt       2160
gaagttgagc ccgcatga                                                     2178

<210> SEQ ID NO 4
<211> LENGTH: 2247
<212> TYPE: DNA
<213> ORGANISM: Unknown
<220> FEATURE:
<223> OTHER INFORMATION: Nucleotide sequence encoding the amino acid
      sequence of OJ1M-273-1; beta-xylosidase candidate gene OJ1M-273-1

<400> SEQUENCE: 4
atgtcggttc gggtgaagga acttttggcg aagatgaccc ttgaggagaa agttgcccaa         60
cttggttcaa tttctgtcca caggctcatg accgacggca aatttgacat tgcaaaggct        120
```

```
cgtgagttgc tcaagcacgg catcggtcaa atcacccgcg tcgctggcgg cagcgattta      180
ccgcctaagg aagcagcaca actcgccaac gaaattcagc gcttcctcat tgaagagacg      240
aggttgggaa ttcccgctat cgtgcacgaa gaatgcctca gcggattgat ggcgcgaggg      300
tcaacgactt tcccccaagc catcaacttg gcaagcactt ttgaccccga tttggttcgg      360
gagatgacaa cggtaattcg caaggaaatg cgcgccgtcg gagcgcatca aggtttgtcg      420
cctgtcttgg atgtccttcg cgacccacga tggggacgga cggaagaaac tttcggcgaa      480
gacccatact tgattgcctg catggcggtc gcttacatct ccggcttgca aggcgaggat      540
ttgaggcagg gcgtcattgc taccgcaaag cacttttcag gtcacggttg gcctgaaggc      600
ggtcgtaact gtgccccact tcatgtcggt ccgagagagt tcagggaagt cctctcattc      660 cccctttgaag cggcagttag ggtggcaaga gttcagtcgg tcatgaacgc ttaccatgac      720
attgatggca tccccctgcgc tgcttcccgc gagttgttga ctgaccttct gcgaggcgaa      780
tggggatttg acggcatcgt cgtttcagat tacgccgccg tccacatgct tttcaatgtc      840
cacagggttg cagttgacga aaaagatgca gcctgccaag cccttatgc aggcattgac       900 attgaactgc ccgacttgaa ctgctacgcc aaattgattg atgccgtccg tgagggacta      960
atttccgagg cgatcgttga cgaggcagtc aggagggttc tcactgtcaa ggaaaggttg     1020
ggcttgtttg acaatccgcc gttcgttgac cccgaagcag caccttccgt ttttgacgcc     1080
cctgaacacc gccaactcgc tcggttgctc gctcaaaagt caattgtgtt gctcaaaaac     1140
gatggtaact tgcttccgct acgaaaagat ttgtcaggca tcgccgtcat cggtccaaac     1200
gccgacgacc cacgaaacat gctcggcgat tacgcttatg tggctcactt ggacttgaag     1260
gaaacgcctg tgccaattgt gactgtcctt gaaggcatca aggcgaaagt ttcacccgcc     1320
acgaaagtcc tttacgccaa aggttgcgaa gttctggacg ggacaacgga aggaatcgcc     1380
gaagcggttg aagtcgcaaa acaagcggaa gtcgttgtct tggtcgtcgg tgaccgctca     1440
ggcttgttcg gcaaagggac ggtcggcgaa ggttgcgata gggttgactt gaggcttccc     1500
ggtcaccaag aggaacttgt caaggctgtg gttgaaactg gcaagcccgt cgtcttggtt     1560
ctcatcaacg gtcgcccgt tacgcttggg gaactcgttg acaaaattcc ggcaatagtt      1620
gaggcttggt ttcccggcga agagggtggt aatgctgttg ctgatgtttt gtttggcgat     1680
gtcaacccag cggcaaaact ccccatcacc ttcccgaaag tcgtcggtca agtcccgctg     1740
cactatagcc gagcaccgct ttcgcaccgc gattatgtgg agatgaaaaa tgtcccgcaa     1800
ttcccattcg ggcacgggct cagttacacg aagtttgaat acagcgactt gacaattgcc     1860
ccagagaaaa tttcacccgc aggcacagtc tccatctccg tgacggtcaa aaatgtcggc     1920
gaccgagaag gtgatgaggt tgtccagttg tatgtccgcg atgtagtcgc aagccgcgtc     1980
cgacccgtca aggaactcaa aggtttcaag cgagtgacgc tgaagccagg tgaggctaaa     2040
cgggtgactt tccacctgtc cgctgaccag ttggcttttt acgaccgagc gatgaggttc     2100
gtggttgagc caggaacaat tgaggtcatg gtcggaagtt cgtctgagga catcaggctc     2160
accggcaaat ttgaaattgt cggcgatgtc agggaagttc caggtgaaag ggtcatgttc     2220
actcaggttg aagttgagcc cgcatga                                         2247
```

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
atgtcggttc gggtgaagga a                                                21

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
tcatgcgggc tcaacttcaa c                                                21

<210> SEQ ID NO 7
<211> LENGTH: 25
<212> TYPE: DNA
<213> ORGANISM: Artificial Sequence
<220> FEATURE:
<223> OTHER INFORMATION: Primer

<400> SEQUENCE: 7
caccatgtcg gttcgggtga aggaa                                            25

<210> SEQ ID NO 8
<211> LENGTH: 29
<212> TYPE: DNA
<213> ORGANISM: Artificial Sequence
<220> FEATURE:
<223> OTHER INFORMATION: Primer

<400> SEQUENCE: 8
tagagctctc atgcgggctc aacttcaac                                        29

<210> SEQ ID NO 9
<211> LENGTH: 752
<212> TYPE: PRT
<213> ORGANISM: Unknown
<220> FEATURE:
<223> OTHER INFORMATION: Beta-xylosidase of Candidatus Caldatribacterium
      californiense

<400> SEQUENCE: 9

Met Ala Leu Val Asn Glu Leu Leu Ser Arg Met Thr Leu Glu Lys
1               5                   10                  15

Val Ala Gln Leu Cys Ala Val His Ala Ser Arg Leu Leu Glu Gly Arg
            20                  25                  30

Lys Phe Ser Glu Glu Lys Ala Arg Thr Val Leu Ala His Gly Ile Gly
        35                  40                  45

Gln Ile Thr Arg Leu Leu Gly Thr Pro Asp Leu Glu Pro Glu Ala
    50                  55                  60

Val Glu Leu Gly Asn Ala Ile Gln Arg Phe Leu Lys Glu Lys Thr Arg
65                  70                  75                  80

Leu Gly Ile Pro Ala Met Ile His Glu Glu Cys Leu Ser Gly Leu Leu
                85                  90                  95

Cys Lys Gly Ala Thr Val Phe Pro Gln Ala Ile Gly Leu Ala Ser Thr
            100                 105                 110

Phe Asn Pro Glu Leu Val Gln Lys Val Thr Thr Ile Arg Lys Thr
        115                 120                 125

Met Arg Ala Leu Gly Val His Gln Gly Leu Ala Pro Val Leu Asp Ile
    130                 135                 140

-continued

```
Pro Arg Asp Pro Arg Trp Gly Arg Thr Glu Thr Phe Gly Glu Asp
145                 150                 155                 160

Pro Tyr Leu Val Ser Arg Met Ala Ser Ala Tyr Ile Arg Gly Leu Gln
            165                 170                 175

Gly Glu Asp Leu Arg Glu Gly Ile Val Ala Thr Ala Lys His Phe Thr
            180                 185                 190

Ala Tyr Gly Ile Ser Glu Gly Gly Arg Asn Leu Ala Pro Ala Lys Val
            195                 200                 205

Gly Glu Arg Glu Leu Arg Glu Val Phe Leu Phe Pro Phe Glu Val Ala
            210                 215                 220

Val Arg Glu Ala Arg Val Arg Ser Leu Met Asn Ala Tyr His Glu Ile
225                 230                 235                 240

Asp Gly Val Pro Cys Ala Ala Ser Ser Phe Leu Leu Thr Lys Val Leu
                245                 250                 255

Arg Glu Glu Trp Gly Phe Glu Gly Ile Val Val Ser Asp Tyr Glu Ala
                260                 265                 270

Val Arg Met Leu Ala Thr Phe His His Val Ala Glu Asp Glu Lys Asp
                275                 280                 285

Ala Ala Val Leu Ala Leu Arg Ala Gly Ile Asp Ile Glu Leu Pro Asp
290                 295                 300

Ala Asp Cys Phe Pro His Leu Val Thr Ala Val Arg Glu Gly Cys Ile
305                 310                 315                 320

Ser Glu Glu Val Leu Asn Glu Ala Val Arg Arg Val Leu Ser Val Lys
                325                 330                 335

Tyr Glu Leu Gly Leu Leu Glu Gly Leu Pro Phe Ala Asp Pro Gly Asn
                340                 345                 350

Val Val Leu Leu Asp Pro Pro Glu His Arg Ala Leu Ser Arg Glu Val
                355                 360                 365

Ala Arg Ala Ala Leu Val Leu Leu Lys Asn Asp Gly Val Leu Pro Leu
370                 375                 380

Lys Lys Asp Leu Arg Ala Leu Ala Val Ile Gly Pro Asn Ala His Asp
385                 390                 395                 400

Pro Ile Asn Leu His Gly Asp Tyr Ser Phe Thr Thr His Val Pro Ser
                405                 410                 415

Val Leu Ala Trp Lys Gly Arg Glu Ala Arg Trp Glu Val Ala Val Pro
                420                 425                 430

Thr Val Thr Val Leu Glu Gly Ile Lys Ala Lys Val Ser Pro Glu Thr
                435                 440                 445

Gln Val Leu Tyr Ala Arg Gly Cys Gly Leu Thr Glu Ser Ser Glu Glu
450                 455                 460

Asp Leu Arg Glu Ala Leu Glu Val Ala Gln Lys Ala Glu Val Ile Val
465                 470                 475                 480

Ala Val Leu Gly Glu Arg Ser Gly Leu Phe Arg Gln Ser Leu Ser Gly
                485                 490                 495

Glu Gly Ser Asp Arg Val Asp Leu Ala Leu Pro Glu Ala Gln Arg Asn
                500                 505                 510

Leu Leu Lys Ala Leu Arg Glu Leu Gly Lys Pro Ile Val Leu Val Leu
                515                 520                 525

Val Asn Gly Arg Pro Leu Glu Leu Leu Trp Glu Tyr Glu His Ile Pro
                530                 535                 540

Ala Ile Leu Glu Ala Trp Tyr Pro Gly Glu Glu Gly Asn Ala Ile
545                 550                 555                 560

Ala Asp Val Leu Phe Gly Asp Tyr Asn Pro Ser Gly Arg Leu Pro Ile
```

-continued

```
              565                 570                 575
Ser Phe Pro Lys Ala Ser Gly Gln Val Pro Val Tyr Tyr Asn Arg Lys
            580                 585                 590

Pro Thr Ser Phe Ser Glu Tyr Val Thr Val Asp Ala Glu Pro Leu Phe
            595                 600                 605

Pro Phe Gly His Gly Leu Ser Tyr Thr Thr Phe Ala Tyr Arg Asp Leu
            610                 615                 620

Arg Ile Ala Pro Glu Lys Val Arg Gly Leu Glu Pro Val Thr Val Gln
625                 630                 635                 640

Cys Thr Val Glu Asn Thr Gly Thr Cys Glu Gly Glu Val Val Gln
                    645                 650                 655

Leu Tyr Leu Arg Asp Lys Val Ala Ser Cys Val Arg Pro Arg Gln Glu
                    660                 665                 670

Leu Lys Gly Phe Val Lys Ile Arg Leu Val Pro Gly Glu Arg Lys Thr
                675                 680                 685

Val Thr Phe Thr Leu Phe Pro Glu Gln Leu Ala Phe Tyr Asp Ala His
            690                 695                 700

Met Arg Phe Val Val Glu Pro Gly Thr Phe Glu Val Met Val Gly Ala
705                 710                 715                 720

Ser Ser Arg Asp Ile Arg Leu Ser Gly Thr Phe Glu Val Leu Glu Glu
                725                 730                 735

Arg Val Ile Pro Lys Tyr Arg His Phe Ala Ser Glu Val Thr Val Gly
                740                 745                 750
```